United States Patent
Ito et al.

(10) Patent No.: US 10,400,226 B2
(45) Date of Patent: Sep. 3, 2019

(54) HIGH FUNCTIONAL ENZYME HAVING MODIFIED SUBSTRATE SPECIFICITY OF HUMAN β-HEXOSAMINIDASE B AND EXHIBITING PROTEASE RESISTANCE

(71) Applicants: TOKUSHIMA UNIVERSITY, Tokushima-shi, Tokushima (JP); MEIJI PHARMACEUTICAL UNIVERSITY, Kiyose-shi, Tokyo (JP)

(72) Inventors: Koji Ito, Tokushima (JP); Hitoshi Sakuraba, Kiyose (JP); Daisuke Tsuji, Tokushima (JP)

(73) Assignees: TOKUSHIMA UNIVERSITY, Tokushima-Shi, Tokushima (JP); MEIJI PHARMACEUTICAL UNIVERSITY, Kiyose-Shi, Tokyo (JP)

( * ) Notice: Subject to any disclaimer, the term of this patent is extended or adjusted under 35 U.S.C. 154(b) by 368 days.

(21) Appl. No.: 14/436,833

(22) PCT Filed: Oct. 17, 2013

(86) PCT No.: PCT/JP2013/078179
§ 371 (c)(1),
(2) Date: Apr. 17, 2015

(87) PCT Pub. No.: WO2014/061735
PCT Pub. Date: Apr. 24, 2014

(65) Prior Publication Data
US 2016/0137994 A1     May 19, 2016

(30) Foreign Application Priority Data
Oct. 19, 2012 (JP) .................. 2012-232266

(51) Int. Cl.
*C12N 9/24* (2006.01)
*A61K 38/47* (2006.01)
*A61K 38/00* (2006.01)

(52) U.S. Cl.
CPC ............ *C12N 9/2402* (2013.01); *A61K 38/47* (2013.01); *C12Y 302/01052* (2013.01); *A61K 38/00* (2013.01)

(58) Field of Classification Search
CPC .................. C12N 9/24; A61K 38/47
See application file for complete search history.

(56) References Cited

U.S. PATENT DOCUMENTS

2005/0064539 A1    3/2005  Chiba et al.

FOREIGN PATENT DOCUMENTS

| JP | 2002-369692 A | 12/2002 | |
|---|---|---|---|
| WO | WO 2010/082622 A1 | 7/2010 | |
| WO | WO-2010082622 | * 7/2010 | ........... C12N 9/2402 |

OTHER PUBLICATIONS

Mark, B. et al., "Crystal Structure of β-Hexosaminidase B: Understanding the Molecular Basis of Sandhoff and Tay-Sachs Disease", *J. Mol. Biol.*, vol. 327, No. 5, Apr. 11, 2003, pp. 1093-1109.

Matsuoka, K. et al., "Functional Improvement of Human β-Hexosaminidase for Purpose of Application to Enzyme Replacement Therapy", *A Summary of Annual Meeting of the Pharmaceutical Society of Japan*, vol. 127, No. 2, 2007, pp. 73. (with English Translation).

Matsuoka, K. et al., "Functional Improvement of Recombinant Human Beta-Hexosaminidase Based on in silico Design", *A Summary of Joint Meeting of the 80th Annual Meeting of the Japanese Biochemical Society and the 30th Annual Meeting of the Molecular Biology Society of Japan*, 2007, pp. 4T7-4. (with English Translation).

Matsuoka, K. et al., "Therapeutic Potential of Intracerebroventricular Replacement of Modified Human β-Hexosaminidase B for GM2 Gangliosidosis", *Molecular Therapy*, vol. 19, No. 6, Jun. 2011, pp. 1017-1024.

Pennybacker, M. et al., "Identification of Domains in Human β-Hexosaminidase That Determine Sustrate Specificity", *The Journal of Biological Chemistry*, vol. 271, No. 29, Jul. 19, 1996, pp. 17377-17382.

Tsuji, D. et al., "Highly Phosphomannosylated Enzyme Replacement Therapy for GM2 Gangliosidosis", *Americal Neurological Association*, vol. 69, No. 4, Apr. 2011, pp. 691-701.

* cited by examiner

*Primary Examiner* — Lynn Y Fan
(74) *Attorney, Agent, or Firm* — Brinks Gilson & Lione

(57) ABSTRACT

Provided is a modified β-subunit of human β-hexosaminidase which has the activity derived from the α-subunit of wild-type human β-hexosaminidase and has the resistance to protease. A protein comprising an amino acid sequence having substitutions of the 312th to the 318th amino acids with glycine, serine, glutamic acid, proline, serine, glycine and threonine in order, respectively, in an amino acid sequence of a β-subunit of wild-type human β-hexosaminidase.

15 Claims, 5 Drawing Sheets
Specification includes a Sequence Listing.

Fig. 1

HEXA (SEQ ID NO:1)
810         820         830         840         850         860         870         880
...atccctggattactgactcctgctactctgggtctgagccctctgcacctttggaccagtgaatcccagt...
    I   P   G   L   L   T   P   C   Y   S   G   S   E   P   S   G   T   F   G   P   V   N   P   S HEXB (SEQ ID NO:3)
870         880         890         900         910         920         930         940
...cagaaagacctcctgactccatgttacagtagacaaaacaagttggactctttggacctataaaccctact...
    Q   K   D   L   L   T   P   C   Y   S   R   Q   N   K   L   D   S   F   G   P   I   N   P   T Mod HEXB (SEQ ID NO:17)
870         880         890         900         910         920         930         940
...cagaaagacctcctgactccatgttacagtgggtctgagccctctggactctttggacctataaaccctact...
    Q   K   D   L   L   T   P   C   Y   S   G   S   E   P   L   D   S   F   G   P   I   N   P   T Modified Mod HEXB (SEQ ID NO:5)
870         880         890         900         910         920         930         940
...cagaaagacctcctgactccatgttacagtgggtctgagccctctggacctctggacctataaaccctact...
    Q   K   D   L   L   T   P   C   Y   S   G   S   E   P   S   G   T   F   G   P   I   N   P   T

HIGH FUNCTIONAL ENZYME HAVING MODIFIED SUBSTRATE SPECIFICITY OF HUMAN β-HEXOSAMINIDASE B AND EXHIBITING PROTEASE RESISTANCE

This application is a 371 application of PCT/JP2013/078179 having an international filing date of Oct. 17, 2013, which claims priority to JP 2012-232266 filed Oct. 19, 2012, the entire contents of which are incorporated herein by reference.

TECHNICAL FIELD

The present invention relates to a recombinant protein having the activity derived from the α-subunit of wild-type human β-hexosaminidase and the resistance to protease.

BACKGROUND ART

Both of Tay-Sachs disease and Sandhoff disease are diseases exhibiting neurological symptoms which are caused by accumulating GM2 ganglioside in neural system cells due to decreased activity of β-hexosaminidase A (Hex A). Hex A is a heterodimer composed of an α-subunit and a β-subunit and has the enzyme activity to degrade GM2 gangliosides. Tay-Sachs disease is a Hex A deficiency caused by α-subunit deficiency and Sandhoff disease is a Hex A deficiency caused by β-subunit deficiency.

The present inventors have previously provided a cell line which was established by introducing an expression vector into which genes encoding an α-subunit and a β-subunit (HEXA cDNA and HEXB cDNA, respectively) are inserted, into CHO cell strains or specific yeast strains and which constitutively expressed a wild-type recombinant Hex A. The present inventors found that the administration of thus produced wild-type recombinant Hex A to Sandhoff disease model mice leads to the reduction of GM2 gangliosides accumulated in neural system cells and the improvement of neurological symptoms, and thus confirmed that an enzyme replacement therapy is efficacious for Tay-Sachs disease and Sandhoff disease (Patent Document 1 and Non-Patent Document 1).

However, in general, in the case where a therapeutic agent containing an enzyme which is deficient is repeatedly administered to a patient, the enzyme in the therapeutic agent is often recognized as a foreign matter in the patient and thus the antibody is produced. Consequently, adverse/side reactions such as allergy reaction and anaphylactic reaction are occurred in the patient. Therefore, in the case where a wild-type recombinant Hex A is directly administered to a patient with Tay-Sachs disease or Sandhoff disease, adverse/side reactions may be occurred in the patient similarly as described above. Furthermore, a wild-type recombinant Hex A has disadvantages such as low stability in blood (plasma) and low ratio of uptake into cells of a disordered organ (neural system cells).

In order to solve these problems, the present inventors produced a modified β-subunit in which the active site of a β-subunit is substituted with the active site of an α-subunit based on conformational information of the α-subunit and β-subunit of β-hexosaminidase. Furthermore, the present inventors produced a modified β-hexosaminidase B which is a homodimer composed of the modified β-subunit (hereinafter, referred to "ModB") and confirmed that the recombinant enzyme has the activity to degrade GM2 gangliosides (Patent Document 2 and Non-Patent Document 2).

PRIOR ART DOCUMENTS

Patent Documents

Patent Document 1: JP 2002-369692 A
Patent Document 2: WO 2010/082622

Non-Patent Documents

Non-Patent Document 1: Tsuji D et al. Ann Neurol. 2011 April; 69(4): 691-701
Non-Patent Document 2: Matsuoka K et al. Mol Ther. 2011 June; 19(6): 1017-1024

SUMMARY OF THE INVENTION

Problems to be Solved by the Invention

Although the present inventors confirmed that in the case where the ModB was administered (singly) to Sandhoff disease model mice, GM2 gangliosides were degraded, the inventors found that the symptoms were not improved in the mice. Then, the present inventors analyzed brain extracts of the mice receiving the ModB and found that the ModB was degraded by protease.

Accordingly, an object of the present invention is to provide a ModB having the resistance to protease.

Solutions to the Problems

As a result of intensive studies to solve the above problems, the present inventors found that the ModB could be obtained which had the resistance to protease by modifying the structure of the site recognized by protease in a β-subunit so as not to be subjected to or not to be susceptible to protease-induced hydrolysis and completed this invention.

That is, the present invention includes the following:

[1] A protein comprising an amino acid sequence having substitutions of the 312th to the 318th amino acids with glycine, serine, glutamic acid, proline, serine, glycine and threonine in order, respectively, in an amino acid sequence of a β-subunit of wild-type human β-hexosaminidase.

[2] The protein according to item [1], further comprising a substitution of the 452nd amino acid with asparagine and/or a substitution of the 453rd amino acid with arginine.

[3] The protein according to item [2], having any one amino acid sequence selected from the following items (i) to (iii):

(i) an amino acid sequence set forth in SEQ ID NO: 6,
(ii) an amino acid sequence having a deletion, a substitution, or an addition of one or a plurality of amino acids excluding the amino acids at said substitution sites in the amino acid sequence shown in SEQ ID NO: 6 and encoding a protein having an activity derived from an α-subunit of wild-type human β-hexosaminidase and having resistance to protease, or
(iii) an amino acid sequence having at least 90% sequence identity to the amino acid sequence set forth in SEQ ID NO: 6 and encoding a protein having the activity derived from the α-subunit of wild-type human β-hexosaminidase and having the resistance to protease (provided that the amino acids at said substitution sites are identical to the amino acids in the amino acid sequence set forth in SEQ ID NO: 6).

[4] A protein consisting of homodimers of the protein according to any one of items [1] to [3].

[5] A gene encoding the protein according to any one of items [1] to [3].

[6] A recombinant vector including the gene according to item [5].

[7] A transfectant including the recombinant vector according to item [6].

[8] A method for producing a protein having an activity derived from α-subunit of wild-type human β-hexosaminidase and having a resistance to protease comprising the steps of culturing the transfectant according to item [7], and collecting the protein from the obtained culture.

[9] A pharmaceutical composition for treating Tay-Sachs disease, characterized by including the protein according to any one of items [1] to [4].

[10] A pharmaceutical composition for treating Tay-Sachs disease, characterized by including the gene according to item [5].

[11] A pharmaceutical composition for treating Sandhoff disease, characterized by including the protein according to any one of items [1] to [4].

[12] A pharmaceutical composition for treating Sandhoff disease, characterized by including the gene according to item [5].

[13] A method for treating Tay-Sachs disease, the method including administrating the protein according to any one of items [1] to [4], the gene according to item [5], or the pharmaceutical composition for treating Tay-Sachs disease according to item [9] or [10] to a patient with Tay-Sachs disease.

[14] A method for treating Sandhoff disease, the method including administrating the protein according to any one of items [1] to [4], the gene according to item [5], or the pharmaceutical composition for treating Sandhoff disease according to item [11] or [12] to a patient with Sandhoff disease.

The present specification embraces the contents described in the specification and/or drawings of JP 2012-232266 A which is the basis of the priority of the present application.

Effects of the Invention

The present invention can provide a ModB having the resistance to protease.

BRIEF DESCRIPTION OF THE DRAWINGS

FIG. 1 shows amino acid sequences and nucleotide sequences including: the amino acid sequence and nucleotide sequence near the region having the protease resistance in the amino acid sequence and nucleotide sequence of the α-subunit of human β-hexosaminidase (HEXA) (SEQ ID NO: 1) (underlined) and the sites corresponding to the region in the amino acid sequence and nucleotide sequence of the β-subunit (HEXB) (SEQ ID NO: 3), the amino acid sequence and nucleotide sequence of the Mod HEXB having the activity derived from the α-subunit (SEQ ID NO: 17), and the amino acid sequence and nucleotide sequence of the protein of the present invention (modified Mod HEXB) (SEQ ID NO: 5). The sites corresponding to the region having the protease resistance of the Mod HEXA are put in a square.

DETAILED DESCRIPTION OF THE PREFERRED EMBODIMENTS

1. Recombinant Protein

Figure 2:
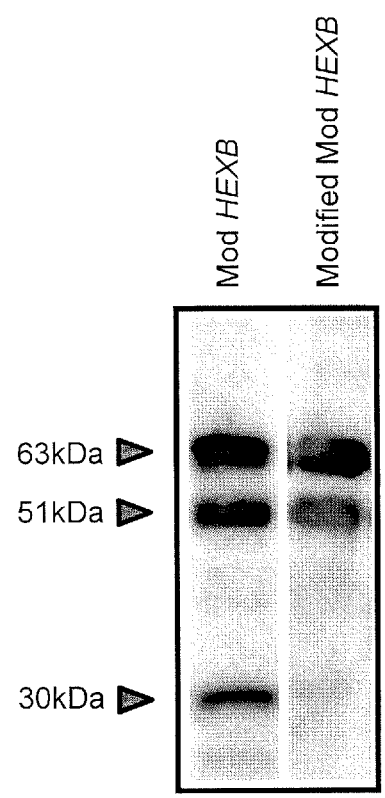
FIG. 2 is a photograph showing detection results of the Mod HEXB and the modified Mod HEXB which were concentrated and purified from a culture supernatant by western blotting. The detected bands of the proteins show precursors of the proteins (approximately 63 kDa), matures of the proteins (approximately 51 kDa), and degraded forms of the proteins (approximately 30 kDa) in the descending order of molecular weights.

The protein of the present invention is a recombinant protein which achieves the activity derived from the α-subunit of wild-type human β-hexosaminidase by modifying the structure of the active site of the β-subunit of wild-type human β-hexosaminidase, and which achieves the resistance to protease by modifying the structure of the protease recognition site of the β-subunit of wild-type human β-hexosaminidase.

Herein, the phrase, "achieves the activity derived from the α-subunit" means that a substrate binding site of the β-subunit exhibits relatively higher biding reactivity with a substrate of the α-subunit than that to a substrate of the β-subunit. Accordingly, a structural change involved in such property is not limited to a structural change which is completely incapable of binding with a substrate of the β-subunit, and also includes a structural change such that the binding reactivity with a substrate of the β-subunit is relatively and significantly higher than that to a substrate of the α-subunit, per se, but the binding reactivity with a substrate of the α-subunit is significantly higher than that to a substrate of the β-subunit, vice versa. Specifically, the phrase, "achieves the activity derived from the α-subunit" preferably includes the substrate specificity of the α-subunit. The phrase, "includes the substrate specificity of the α-subunit" means that the structure of an active site (especially, a position and type of amino acid residue which serves importantly for the binding reactivity of a substrate) and the occurrence of a loop structure required for association (binding) with a GM2 activator are similar to those of α-subunit.

Additionally, the phrase, "achieve the resistance to protease" means that the structural change of the protease recognition site allows the recombinant protein not to be subjected to or not to be susceptible to protease-induced hydrolysis (i.e., not to be hydrolyzed or not to be easily hydrolyzed).

The structural change of the protein involved in such property can be carried out as follows.

A structural change of the active site of the β-subunit to achieve the activity derived from the α-subunit can be carried out according to the procedure detailed in WO 2010/082622.

That is, the structural change can be carried out by identifying an amino acid residue within an active pocket to recognize GM2 gangliosides as a substrate, and an amino acid residue involved in the binding with a GM2 activator (served for the association of the enzyme with the substrate itself, GM2 gangliosides) in the α-subunit based on X-ray crystal structural information of the human Hex A (heterodimer composed of the α-subunit and the β-subunit) and Hex B (homodimer of the β-subunit), and substituting the corresponding moiety to these specific amino acid residues with specific amino acid residues identified in the α-subunit in the β-subunit molecule. Herein, it is noted that the term, "the corresponding moiety" means a position which is aligned in parallel by inserting a gap to one sequence of amino acid sequences, as needed so as to achieve the highest identity between amino acid sequences of the α-subunit and β-subunit. An alignment of amino acid sequences can be carried out by using a method well known by those skilled in the art such as sequence analysis software (e.g., BLAST (Basic Local Alignment Search Tool at the National Center for Biological Information))(e.g., default, i.e., parameters in initial setting).

In the β-subunit, the corresponding moiety to an amino acid residue within an active pocket to recognize, as a substrate, GM2 gangliosides of the α-subunit includes the 452nd amino acid residue and the 453rd amino acid residue. In the β-subunit, amino acid residues involved in the binding with a GM2 activator of the α-subunit include the 312th to 315th amino acid residues.

In the case where the protein of the present invention achieves the activity derived from the α-subunit, the 312th to the 315th amino acid residues in the β-subunit may be substituted. Preferably, in the case where the protein of the present invention achieves the activity derived from the α-subunit, the 312th to the 315th amino acid residues and the 452nd amino acid residue and/or the 453rd amino acid residue in the β-subunit may be substituted. More preferably, in the case where the protein of the present invention achieves the activity derived from the α-subunit, the 312th to the 315th amino acid residues, the 452nd amino acid residue and the 453rd amino acid residue in the β-subunit may be substituted.

Such substitution of the amino acid sequence in the β-subunit can be carried out based on the amino acid residues of the corresponding moiety in the α-subunit, that is, the 312th to the 315th amino acids are substituted with glycine, serine, glutamic acid, and proline in order, respectively, and the 452nd amino acid is substituted with asparagine, as well as the 453rd amino acid of amino acid is substituted with arginine.

A structural change of the active site in the β-subunit to achieve the resistance to protease can be carried out by introducing after substituting a protease non-recognition site with the protease recognition site of the β-subunit. Herein, the term, "protease recognition site" means an amino acid sequence which is hydrolyzed by a specific protease. In the present invention, the introduction of a protease non-recognition site into the protease recognition site of the β-subunit can be carried out, for example, by introducing after substituting a region known to have the resistance to protease in the α-subunit with the corresponding moiety to the region in the β-subunit.

In the β-subunit, amino acid residues corresponding to a protease non-recognition site of the α-subunit include the 312th to the 318th amino acid residues. In the case where the protein of the present invention achieves the resistance to protease, at least the 312th to the 318th amino acid residues in the β-subunit may be substituted.

Such substitution of the amino acid sequence in the β-subunit can be carried out based on the amino acid residues of the corresponding moiety in the α-subunit (FIG. 1), that is, the 312th to the 315th amino acids are substituted with glycine, serine, glutamic acid and proline in order, respectively, and the 316th to the 318th amino acids are substituted with serine, glycine and threonine in order, respectively, as described above.

The substitution of at least the 312th to the 318th amino acids in the β-subunit in the above-described manner can provide effects such that the protein is not recognized by protease, i.e., is not subjected to or not susceptible to hydrolysis by protease.

Accordingly, the protein of the present invention is a protein in which the 312th to the 318th amino acids of the amino acid sequence in the β-subunit are substituted with glycine, serine, glutamic acid, proline, serine, glycine and threonine in order, respectively. In the protein of the present invention, the 452nd amino acid and/or the 453rd amino acid may be further substituted with asparagine and arginine, respectively. Preferably, the protein of the present invention is a protein in which the 312th to the 318th, the 452nd and the 453rd amino acids of the amino acid sequence in the β-subunit are substituted as described above, respectively.

Information of the amino acid sequence in the β-subunit (SEQ ID NO: 4) and the nucleotide sequence encoding the sequence (SEQ ID NO: 3) is published, for example, as "Accession number: NM 000512" and "Accession number: NM 000521" in GenBank and is registered as "Entry name: HEXB-HUMAN; Accession number: P07686" in Swiss-Prot (available from http://tw.expasy.org/uniprot/). Additionally, information of the amino acid sequence in the α-subunit (SEQ ID NO: 2) and the nucleotide sequence encoding the sequence (SEQ ID NO: 1) is also published, for example, as "Accession number: NM 000511" and "Accession number: NM 000520" in GenBank and is registered as "Entry name: HEXA-HUMAN; Accession number: P06865" in Swiss-Prot (available from http://tw.expasy.org/uniprot/), as well. In this case, the nucleotide sequence encoding the amino acid sequence in the α-subunit (cDNA) set forth in SEQ ID NO: 1 is the nucleotide sequence composed of the 208th to the 1797th nucleotides in the nucleotide sequence having 2437 bp in total, as published by GenBank (Accession number: NM 000520). Similarly, the nucleotide sequence encoding the amino acid sequence in the β-subunit (cDNA) set forth in SEQ ID NO: 3 is the nucleotide sequence composed of the 118th to the 1788th nucleotides in the nucleotide sequence having 1919 bp in total, as published by GenBank (Accession number: NM 000521).

In the present invention, information of these amino acid sequences and nucleotide sequences can be utilized.

Specifically, the protein of the present invention is the following proteins of items (a) to (c).

(a) A protein including any one amino acid sequence of the following items (i) to (iv).

(i) an amino acid sequence having substitutions of the 312th to the 318th amino acids with glycine, serine, glutamic acid, proline, serine, glycine and threonine in order, respectively, in an amino acid sequence set forth in SEQ ID NO: 4;

(ii) an amino acid sequence having substitutions of the 312th to the 318th amino acids with glycine, serine, glutamic acid, proline, serine, glycine and threonine in order, respectively, and a substitution of the 452nd amino acid with asparagine in an amino acid sequence set forth in SEQ ID NO: 4;

(iii) an amino acid sequence having substitutions of the 312th to the 318th amino acids with glycine, serine, glutamic acid, proline, serine, glycine and threonine in order, respectively, and a substitution of the 453rd amino acid with arginine in an amino acid sequence set forth in SEQ ID NO: 4; or (iv) an amino acid sequence having substitutions of the 312th to the 318th amino acids with glycine, serine, glutamic acid, proline, serine, glycine and threonine in order, respectively, a substitution of the 452nd amino acid with asparagine and a substitution of the 453rd amino acid with arginine in an amino acid sequence set forth in SEQ ID NO: 4; or (b) a protein comprising an amino acid sequence having a deletion, a substitution, or an addition of one or a plurality of amino acids excluding the amino acids at the substitution sites in the amino acid sequence of any one amino acid sequence of the items (i) to (iv) and having the activity derived from the α-subunit of wild-type human β-hexosaminidase and having the resistance to protease, or (c) a protein comprising an amino acid sequence having at least 90% sequence identity to any one amino acid sequence of the items (i) to (iv) (provided that the amino acids at the substitution sites are identical to the amino acid sequence set forth in SEQ ID NO: 6), and having the activity derived from the α-subunit of wild-type human β-hexosaminidase and having the resistance to protease.

In the protein of the item (a), among proteins including the amino acid sequence of the items (i) to (iv), the protein including the amino acid sequence of the item (iv) is more preferred. An example of these proteins includes the protein including the amino acid sequence set forth in SEQ ID NO: 6, and the protein composed of the amino acid sequence set forth in SEQ ID NO: 6 is preferred.

The protein of the item (b) may be, but is not limited to, a protein comprising an amino acid sequence having a deletion, a substitution, or an addition, of one or a plurality (e.g., about one to ten, preferably about one to five) of amino acids excluding the amino acids at the substitution sites in any one amino acid sequence of the items (i) to (iv) included in the protein of the item (a) and having the activity derived from the α-subunit and having the resistance to protease. The deletion, substitution or addition is preferably carried out in a moiety excluding a signal peptide of the β-subunit. The signal peptide is the moiety composed of the 1st to the 54th amino acids in the amino acid sequence set forth in SEQ ID NO: 4.

The activity derived from the α-subunit can be confirmed by expressing the target protein in cells derived from mammals such as CHO cells or human fibroblast cells and then collecting the expressed protein, and measuring the 4-MUGS degradation activity of the resultant protein. In particular, the activity can be measured as follows: the protein (enzyme solution) and 4-methylumbelliferyl-6-sulfo-N-acetyl-β-D-glucosaminide (artificial substrate) are mixed and reacted with each other under the condition of pH 4.5 and then 4-methylumbelliferone is produced. An amount of the produced 4-methylumbelliferone, which may be released per unit time from a unit amount of the enzyme solution, is detected. 4-Methylumbelliferone can be detected by adopting various known detection methods, for example, preferably a detection method including the use of a fluorometer. The expression of the target protein can be made by introducing into a cell after incorporating into an expression vector such as various known expression vectors.

The presence or absence of the resistance to protease is determined for example, by expressing the target protein in a cell derived from mammals such as CHO cells or human fibroblast cells and then collecting the expressed protein, and detecting the protein in the hydrolyzed form by a known method for detecting proteins such as western blotting.

The protein of the item (c) may be, but is not limited to, a protein which includes an amino acid sequence having an identity of at least 90% or more to the amino acid sequence of the items (i) to (iv) included in the protein of the item (a) and has the activity derived from the α-subunit of wild-type human β-hexosaminidase and has the resistance to protease (provided that the amino acids at the substitution sites are identical to the amino acid sequence set forth in SEQ ID NO: 6). Herein, the term, "identity" means a percentage of amino acid residues identical to and amino acid residues similar to each other between two amino acid sequences based on total amino acid residues, wherein the two amino acid sequences are aligned with or without gap introduction and overlapped in optional alignment. The identity can be determined by using a method well known to those skilled in the art such as sequence analysis software (e.g., BLAST (Basic Local Alignment Search Tool at the National Center for Biological Information)) (e.g., default, i.e., parameters in initial setting). The term, "identity of at least 90% or more" represents the identity of 90% or more, preferably 95% or more, more preferably 99% or more. The presence or absence of "the activity derived from the α-subunit" and "resistance to protease" can be determined in the above-described manner.

The protein of the present invention may be the form of a monomer (i.e., modified (mutant) β-subunit) or the form of a dimer of the mutant protein (i.e., modified (mutant) human β-hexosaminidase).

2. Recombinant Gene

The recombinant gene of the present invention is not limited as far as it is a gene encoding the above-described protein. Examples of such a gene include a gene including DNA of the following item (a) or (b).

(a) A DNA including any one nucleotide sequence of the following items (i) to (iv), (i) a nucleotide sequence having substitutions of the 934th to the 936th nucleotides, the 937th to the 939th nucleotides, the 940th to the 942nd nucleotides, the 943rd to the 945th nucleotides, the 946th to the 948th nucleotides, the 949th to the 951st nucleotides and the 952nd to the 954th nucleotides with nucleotides representing codons for glycine, serine, glutamic acid, proline, serine, glycine and threonine in order, respectively, in a nucleotide sequence shown in SEQ ID NO: 3;

(ii) a nucleotide sequence having substitutions of the 934th to the 936th nucleotides, the 937th to the 939th nucleotides, the 940th to the 942nd nucleotides, the 943rd to the 945th nucleotides, the 946th to the 948th nucleotides, the 949th to the 951st nucleotides and the 952nd to the 954th nucleotides with nucleotides representing codons for glycine, serine, glutamic acid, proline, serine, glycine and threonine in order, respectively and a substitution of the 1354th to the 1356th nucleotides with nucleotides representing a codon for asparagine in a nucleotide sequence shown in SEQ ID NO: 3;

(iii) a nucleotide sequence having substitutions of the 934th to the 936th nucleotides, the 937th to the 939th nucleotides, the 940th to the 942nd nucleotides, the 943rd to the 945th nucleotides, the 946th to the 948th nucleotides, the 949th to the 951st nucleotides and the 952nd to the 954th nucleotides with nucleotides representing codons for glycine, serine, glutamic acid, proline, serine, glycine and threonine in order, respectively and a substitution of the 1357th to the 1359th nucleotides with nucleotides representing a codon for arginine in a nucleotide sequence shown in SEQ ID NO: 3;

(iv) a nucleotide sequence having substitutions of the 934th to the 936th nucleotides, the 937th to the 939th nucleotides, the 940th to the 942nd nucleotides, the 943rd to the 945th nucleotides, the 946th to the 948th nucleotides, the 949th to the 951st nucleotides and the 952nd to the 954th nucleotides with nucleotides representing codons for glycine, serine, glutamic acid, proline, serine, glycine and threonine in order, respectively and a substitution of the 1354th to the 1356th nucleotides with nucleotides representing a codon for asparagine as well as a substitution of the 1357th to the 1359th nucleotides with nucleotides representing a codon for arginine in a nucleotide sequence shown in SEQ ID NO: 3.

(b) a DNA hybridized with a DNA composed of the complementary nucleotide sequence to a DNA including any one nucleotide sequence of the items (i) to (iv) under a stringent condition, wherein the DNA encodes a protein in which the corresponding nucleotides to nucleotides at the substitution sites are identical to nucleotides at the substitution sites and which has the activity derived from the α-subunit of wild-type human β-hexosaminidase and the resistance to protease.

The term, "codon" in the present invention is not limited to a triplet on an RNA sequence after transcription and also means a triplet on a DNA sequence. Thus, in a codon on the DNA sequence, thymine (T) is denoted instead of uracil (U).

The nucleotide sequence set forth in SEQ ID NO: 3 is a nucleotide sequence composed of 1671 nucleotides encoding the β-subunit of wild-type human β-hexosaminidase (556 amino acids).

In the DNA of the item (a), among DNAs including nucleotide sequences of the items (i) to (iv), a DNA including a nucleotide sequence of the item (iv) is preferred. Examples of such DNA include a DNA including a nucleotide sequence set forth in SEQ ID NO: 5, preferably a DNA composed of the nucleotide sequence set forth in SEQ ID NO: 5.

A substituted mutant DNA as described above can be prepared for example, by known site-directed mutagenesis described in Molecular Cloning, A Laboratory Manual 2nd ed., Cold Spring Harbor Laboratory Press (1989), Current Protocols in Molecular Biology, John Wiley ? (1987-1997) and the like (e.g., Kunkel method, Gapped duplex method, and PCR method).

In the DNA of the item (b), the term, "stringent condition" is a condition when washing after hybridization, and means a condition of a buffer salt concentration of 15-330 mM and a temperature of 25-65° C., preferably a buffer salt concentration of 15-150 mM and a temperature of 45-55° C. A particular example includes a condition of 80 mM and 50° C.

A hybridized DNA preferably includes a nucleotide sequence having a homology of at least 40% or more, more preferably 60%, still more preferably 90% or more, particularly preferably 95% or more, most preferably 99% or more to the nucleotide sequence of the DNA of the item (a).

In the DNA of the item (b), the corresponding nucleotides to the nucleotides at the substitution sites are identical to the nucleotides at the substitution sites. Herein, the term, "the corresponding nucleotides" of "the corresponding nucleotides to the nucleotides at the substitution sites" means nucleotides (triplet) positionally opposed to the complementary nucleotides (triplet) to the nucleotides at the substitution sites in a hybrid obtained by hybridization of the DNA of the item (b) with the complementary chain to the DNA of the item (a).

Furthermore, in the DNA of the item (b), the nucleotide sequence region encoding a signal peptide of the β-subunit is preferably identical to one of the DNA of the item (a). The nucleotide sequence region encoding the signal peptide is the region composed of the 1st to the 162nd nucleotides in the nucleotide sequence set forth in SEQ ID NO: 3.

The DNA of the item (b) is particularly preferably a DNA composed of a nucleotide sequence such that nucleotide sequences are not completely identical to each other, but amino acid sequences after translation are completely identical to each other compared with the DNA of the item (a) (i.e., the DNA of the item (a) in which a silent mutation was engineered).

In the recombinant gene of the present invention, the corresponding codon to individual amino acids after translation is not particularly limited and may be one including a DNA including a codon generally used in mammals such as human (preferably a codon frequently used) after transcription or one including a DNA including a codon generally used in microorganism such as Escherichia coli and yeast and plants (preferably a codon frequently used).

The recombinant gene of the present invention may include a known nucleotide sequence required for gene expression (transcriptional promoter, SD sequence, Kozak sequence, terminator or the like) in addition to the above-described DNA.

3. Recombinant Vector and Transfectant

A recombinant vector of the present invention can be constructed by incorporating the recombinant gene of the present invention described above into an appropriate expression vector. In this case, the gene to be incorporated into an expression vector may be previously linked to a transcriptional promoter, a SD sequence (as a host is prokaryotic cells) and Kozak sequence (as a host is eukaryotic host cells) at the upstream, or linked to a terminator at the downstream, as well as linked to an enhancer, a splicing signal, a poly A addition signal, a selection marker or the like as needed. It is noted that elements required for gene expression such as the transcriptional promoter may be originally included in the gene or in the case where the elements are originally included in an expression vector, they may be used, and the aspect of use of the elements is not particularly limited.

Various methods including the use of a known genetic recombination technology such as a method including the use of a restriction enzyme or a method including the use of topoisomerase can be adopted as a method for incorporating the gene into an expression vector. Examples of the expression vector include, but are not limited to, a plasmid DNA, a bacteriophage DNA, a retrotransposon DNA, a retrovirus vector, and an artificial chromosome DNA, as far as the vector may retain a gene encoding the protein of the present invention, and a vector suitable for a host cell to be used can be appropriately selected and used.

Then, the recombinant vector constructed in the above-described manner can be introduced into a host to obtain a transfectant, and the obtained transfectant is cultured, followed by expressing the protein of the present invention. It is noted that the term, "transfectant" as used in the present invention means a transformant in which a foreign gene is introduced into a host, and examples thereof include one in which a foreign gene is introduced through the introduction of a plasmid DNA, etc., into a host (transfection), and one in which a foreign gene is introduced through the infection of various viruses and phages into a host (transduction).

A host is not limited as far as the recombinant vector is introduced thereinto and then the protein of the present invention may be expressed. A host can be appropriately selected, and examples thereof include known hosts such as various animal cells such as human and mouse, various plant cells, bacteria, yeasts, and plant cells.

In the case where animal cells are a host, human fibroblasts, CHO cells, cultured cells derived from baby hamster kidney (BHK cells), monkey cells COS-7, Vero, mouse L cells, rat GH3 and human FL cells are used, for example. Additionally, insect cells such as Sf9 cells and Sf21 cells can be also used. In the case where bacteria are a host, *Escherichia coli* and *Bacillus subtilis* are used, for example. In the case where yeasts are a host, *Saccharomyces cerevisiae* and *Schizosaccharomyces pombe* are used, for example. In the case where plant cells are a host, tobacco BY-2 cells are used, for example.

A method for obtaining a transfectant is not limited and can be appropriately selected with consideration for a combination of any types of a host and an expression vector, examples of the method preferably including electroporation, lipofection, heat shock method, PEG method, calcium phosphate method, DEAE-dextran method and a method including the infection by various viruses such as DNA virus and RNA virus.

In the obtained transfectant, the codon type of a gene included in a recombinant vector may be matched with or different from the codon type of a host to be actually used, and is not limited.

4. Method for Producing Protein

In particular, the production of the protein of the present invention can be carried out by a method including the steps of culturing the above-described transfectant and collecting a protein having the activity derived from the α-subunit and having the resistance to protease from the obtained culture. Herein, the term, "culture" means any of a culture supernatant, a cultured cell, a cultured fungous form or a disrupted matter of a cell or a fungous form. The cultivation of the transfectant can be carried out according to an ordinary method used in the cultivation of a host. The target protein is accumulated in the culture.

As far as a medium to be used in the cultivation contains sources of carbon, nitrogen and inorganic salts, etc., which may be assimilated by a host and can effectively culture a transfectant, any of various known natural media and synthetic media may be used.

In order to prevent shedding of a recombinant vector contained in a transfectant and a gene encoding the target protein during culturing, the cultivation may be carried out under selective pressure. That is, in the case where a selective marker is a drug resistant gene, the corresponding drug can be added to a medium, and in the case where a selective marker is an auxotrophic complementary gene, the corresponding nutritional factor can be removed from a medium. For example, in the case where human fibroblasts transduced by a vector containing G418 resistant gene is cultured, G418 (G418 sulfate) may be added to a medium during the cultivation, as needed.

In the case where a transfectant and the like obtained by introducing an expression vector including an inducible promoter as a promoter is cultured, a suitable inducer (e.g., IPTG) may be added to a medium, as needed.

The condition for culturing a transfectant is not particularly limited as far as the production of the target protein and the growth of the host are not hindered, and the cultivation is carried out at 10° C.-40° C., preferably 20° C.-37° C. for 5-100 hours. The pH can be adjusted with inorganic or organic acid, alkali solution and the like. Examples of a method for culturing include solid-state culture, static culture, shaking culture, aeration/agitation culture.

In the case where the target protein is produced inside a fungous form or a cell after culturing, the target protein can be collected by disrupting the fungous form or the cell. High pressure treatment by French press or homogenizer, ultrasonication, grinding treatment by glass beads, etc., enzymatic treatment with lysozyme, cellulase, or pectinase, etc., freezing and thawing treatment, hypotonic treatment, phage-induced lysis treatment, and the like can be utilized as a method for disrupting fungous forms or cells. After disrupting, disrupted residues of a fungous form or a cell (including insoluble fragments of a cell extract) can be removed, as needed. Examples of a method for removing residues include centrifugation and filtration, and a coagulant, a filter aid, etc. can be also used to increase residue removal efficiency, as needed. The supernatant obtained after removing residues is soluble fragments of the cell extract and can be used as a partially purified protein solution.

In the case where the target protein is produced inside a fungous form or a cell, the fungous form and the cell themselves are collected by centrifugation, membrane separation or the like and then the fungous form and the cell in the undisrupted form may be directly used.

On the other hand, in the case where the target protein is produced outside a fungous form or a cell, the culture broth is directly used or the fungous form or the cell is removed by centrifugation, filtration or the like. Subsequently, the target protein is collected from the culture through the extraction by ammonium sulfate precipitation or the like, as needed, and then the obtained target protein can be also subjected to the isolation and purification by dialysis, various chromatographies (e.g., gel permeation, ion exchange chromatography and affinity chromatography), as needed.

The production yield of the protein obtained by culturing a transfectant, etc. can be confirmed in a unit such as per culture broth, per fungous form wet weight or dry weight, or per protein of a crude enzymatic solution through SDS-PAGE (Poly Acrylamide Gel Electrophoresis).

The production of the target protein can be also carried out by cell free protein synthesis system with no living cell in addition to the protein synthesis system with a transfectant as described above. The cell free protein synthesis system is a system for synthesizing the target protein with a cell extract in an artificial container such as a test tube. An example of a cell free protein synthesis system able to be used also includes a cell free transcription system wherein RNA is synthesized from DNA used as a genetic template.

In this case, a cell extract to be used is preferably derived from the host cell described above. For example, an extract derived from eukaryotic cells or prokaryotic cells, more particularly, CHO cells, rabbit reticulocyte, mouse L-cells, Hela cells, wheat malts, budding yeasts, *Escherichia coli*, etc., can be used as a cell extract. It is noted that these cell extracts may be used after concentration or dilution or used directly, which are not limited. A cell extract can be obtained, for example, by ultrafiltration, dialysis, polyethylene glycol (PEG) precipitation. The target protein produced by a cell free protein synthesis system can be purified by a means appropriately selected such as chromatography as described above.

5. Pharmaceutical Composition

(i) Pharmaceutical Composition as Supplemental Enzyme Drug, Etc.

Since the protein of the present invention has the activity derived from the α-subunit and exhibits the resistance to protease, the protein may provide excellent effects for treatments for Tay-Sachs disease and Sandhoff disease and can be used as an active component in therapeutic agents of Tay-Sachs disease and Sandhoff disease. That is, the present invention provides pharmaceutical compositions for treating Tay-Sachs disease (therapeutic agent for Tay-Sachs disease) and Sandhoff disease (therapeutic agent for Sandhoff disease), which contain the protein of the present invention described above. These pharmaceutical compositions are particularly preferably a supplemental enzyme drug usable for enzyme supplementation therapy. It is noted that the protein of the present invention used for these pharmaceutical compositions is particularly preferably a homodimer. Furthermore, the homodimer composed of the protein of the present invention can be obtained by associating with the proteins, and for example, the protein of the present invention, which is expressed in a cell into which a gene encoding the protein of the present invention is introduced, can form a homodimer by spontaneously associating with the proteins each other in the cell.

The protein of the present invention, which is an active component in the pharmaceutical composition, may be used in the form of various salts, hydrates, etc., as needed, or in the form of optimal chemical modification in consideration of the preservation stability (especially, the maintenance of activity) as a therapeutic agent, which form is not limited.

The pharmaceutical composition can include another component besides the protein of the present invention. Examples of the other component include various pharmaceutical components (various pharmaceutically acceptable carriers) required depending on the use (the use form) of the pharmaceutical composition. The other component can be appropriately contained within the range not to impair effects provided by the protein of the present invention or the like.

In the case where the pharmaceutical composition is used in a supplemental enzyme drug, a blending proportion of the protein of the present invention and a type or blending proportion of the other component can be appropriately set according to a known method for preparing a supplemental enzyme drug.

A method for administrating the pharmaceutical composition is not limited, however, in the case of a supplemental enzyme drug, parenteral administration methods such as intravenous drip infusion, intrathecal injection, and intraventricular administration are usually adopted. A preparation usable for various administration methods such as parenteral administration methods can be prepared according to an ordinary method in which an excipient, a filler, an expander, a binder, a wetting agent, a disintegrant, a lubricant, a surfactant, a dispersant, a buffer, a preservative, a solubilizer, an antiseptic agent, a corrigent, a soothing agent, a stabilizer, a tonicity agent and the like which are generally used in drug productions are appropriately selected and used.

The form of the pharmaceutical composition is not limited, however, in the case of a supplemental enzyme drug, an intravenous injectable preparation (including drip infusion) is usually adopted and may be provided for example, in the form of a unit dose ampoule or a multi-dose container.

Generally, the dose of the pharmaceutical composition can be appropriately set in a broad range in view of the blending proportion of an active component in the preparation as well as the age, body weight, type of disease, medical condition of a subject to be administrated (patient), and the route, frequency and period of administration, and the like. In particular, in the case where the therapeutic agent of the present invention is a supplemental enzyme drug, the frequency of administration is preferably about once per 2-4 weeks and the dose (/once) is preferably an amount capable of administrating about 0.1-10 mg/kg, more preferably about 0.1-5 mg/kg, still more preferably about 0.2-1 mg/kg of the protein of the present invention (recombinant enzyme), etc., serving as an active component relative to the body weight of the patient, for example.

In the present invention, since the protein of the present invention serving as an active component (recombinant enzyme) exhibits the protease resistance as well as has excellent stability in blood and cerebrospinal fluid and high ratio of uptake into cells of a disordered organ, even in using low amount of the protein, excellent enzyme supplemental effects similar to or greater than the conventional basic effect can be obtained. Additionally, since the protein has extremely low adverse effect such as allergic side effect, physical, mental and economic stresses of the patient can be significantly reduced. A continuous administration of the protein of the present invention (preferably, continuous intrathecal or intraventricular administration) allows to treat or improve central nerve symptoms occurred in Tay-Sachs disease and Sandhoff disease.

(ii) Pharmaceutical Composition as Gene Therapeutic Agent

The gene of the present invention encodes the protein of the present invention capable of providing various excellent effects on the treatments of Tay-Sachs disease and Sandhoff disease, as described above, and can be used as active components of pharmaceutical compositions for treating Tay-Sachs disease (Tay-Sachs disease therapeutic agent (particularly, gene therapeutic agent)) and of pharmaceutical compositions for treating Sandhoff disease (Sandhoff disease therapeutic agent (particularly, gene therapeutic agent)).

In the case where the pharmaceutical composition (gene therapeutic agent) is used, examples thereof include a method including direct administration via an injection as well as a method including the administration of a vector into which a nucleic acid is incorporated. Examples of the vector include an adenovirus vector, an adeno associated virus vector, a herpes virus vector, a vaccinia virus vector, a retrovirus vector and a lentivirus vector. The use of these virus vectors allows an effective administration of the composition.

In the case where the pharmaceutical composition (gene therapeutic agent) is used, examples thereof may also include a method including introducing the composition into an endoplasmic reticulum of phospholipid such as liposome, and then administrating the obtained endoplasmic reticulum. The endoplasmic reticulum retaining the gene of the present invention is introduced into predetermined cells by lipofection method. Subsequently, the obtained cells are, for example, intravenously or intraarterially administrated. Alternatively, the obtained cells can be locally administrated to or implanted in a disordered organ of Tay-Sachs disease or Sandhoff disease. Stem cells derived from a patient (e.g., hematopoietic stem cells, hematopoietic precursor cells, mesenchymal stem cells, etc.) can be used as the cells and these cells into which the gene of the present invention is introduced and cell strains derived from these cells can be administrated to/implanted in the patient. For example, in the case where the pharmaceutical composition is administrated to an adult, the dose amount is preferably about 0.1 µg/kg-1000 mg/kg, more preferably about 1 µg/kg-100 mg/kg per day relative to the body weight of the patient. The central nerve symptoms can be treated or improved by the following: the gene of the present invention is introduced into cells in the brain and then the protein of the present invention is expressed therein, or cells into which the gene of the present invention is introduced is transferred to the brain or the cells are implanted in the brain and then the protein of the present invention is expressed therein.

Most of the molecular structure (particularly, outer shell) of the protein of the present invention is equivalent to the molecular structure of the β-subunit and therefore, even in the case where the protein is used for a patient with Tay-Sachs disease, who has a β-subunit, but has no α-subunit, an allergy reaction may not likely be caused.

Generally, HexB is known which has higher stability than Hex A and which has more sugar chains than Hex A and therefore, HexB is easily taken up into cells of neural system via mannose 6-phosphate receptors on cell membranes. Accordingly, a homodimer composed of the protein of the present invention has also higher stability and higher ratio of uptake into cells of a neural system as compared with wild-type Hex A, and therefore can provide high clinical effects. In view of this, the protein is believed to be efficacious not only as a therapeutic agent for Tay-Sachs disease, but also as a therapeutic agent for Sandhoff disease.

6. Treatment Method

The present invention includes a method for treating Tay-Sachs disease or Sandhoff disease, characterized by administrating the above-described pharmaceutical composition to a patient with Tay-Sachs disease or Sandhoff disease. Also, the present invention includes the use of the pharmaceutical composition or the protein and/or gene of the present invention for treating Tay-Sachs disease or Sandhoff disease, as well as the use of the pharmaceutical composition or the protein and/or gene of the present invention in the manufacture of a drug for treating Tay-Sachs disease or Sandhoff disease.

The pharmaceutical composition to be used in the treatment method of the present invention may be, but is not limited to, a pharmaceutical composition including the protein of the present invention (the above section, "5. (i)"; supplemental enzyme drug), a pharmaceutical composition including the gene of the present invention (the above section, "5. (ii)"; gene therapeutic drug), or a mixture of these pharmaceutical compositions, and can be appropriately selected in consideration of the medical condition of the patient, the presence or absence of side effects, effects of the administration, etc.

In particular, in the case where the mixture is used, the proportion of dose, the frequency and period of the administration of each pharmaceutical composition, etc., can be appropriately set depending on individual patient. Preferred administration method and dose, etc., of each pharmaceutical composition is as defined above.

Hereinafter, the present invention will be more particularly described by way of Examples, but the present invention is not limited thereto.

EXAMPLES

Example 1: Preparation of a Modified β-Subunit Having the Activity Derived from an α-Subunit and the Protease Resistance A recombinant gene encoding a modified β-subunit which is composed of an amino acid sequence comprising substitutions at the 312th to the 315th amino acids with glycine, serine, glutamic acid and proline in order, respectively and a substitution at the 452nd amino acid with asparagine and a substitution at the 453rd amino acid with arginine in an amino acid sequence of β-subunit, and which has the activity derived from an α-subunit (hereinafter, described as "Mod HEXB") was produced according to a known procedure (WO2010/082622). The obtained recombinant gene (SEQ ID NO: 17) was incorporated into a pCXN₂ vector (pCXN₂-Mod HEXB).

Subsequently, in order to obtain a modified Mod HEXB including the corresponding moiety to the region, the region of the α-subunit known to have the protease resistance (the region underlined in FIG. 1) was subjected to PCR method with the following four primers, which used a pCXN₂-Mod HEXB as a genetic template, to obtain a Mod HEXB gene into which the gene encoding the region was introduced (i.e., "modified Mod HEXB gene" (SEQ ID NO: 5)).

```
                                        (SEQ ID NO: 7)
5'-AAAGAATTCCTCGAGCACCATGCTGCTGGCGCTG-3'

(SEQ ID NO: 8)
5'-GGTGCCAGAGGGCTCAGACCCACTGTAACATGGAGTCAG-3'

(SEQ ID NO: 9)
5'-GAGCCCTCTGGCACCTTTGGACCTATAAAC-3'

(SEQ ID NO: 10)
5'-GAGGGAAAAAGATCTTACATGTTCTCATG-3'
```

The obtained modified Mod HEXB gene was incorporated into a pCXN₂ vector with In-Fusion HD Cloning Kit (TAKARA BIO INC.) to produce a modified Mod HEXB expression vector.

Sequencing of the modified Mod HEXB gene was carried out with DTCS Quick Start Master Mix (Beckman Coulter, Inc.). Sequencing reaction was carried out with the following primers according to the manufacturer's instruction and then analyzed by CEQ8000 (Beckman Coulter, Inc.). Consequently, the fact was confirmed that the modified Mod HEXB gene includes a DNA encoding the region known to have the protease resistance in an α-subunit.

```
                                        (SEQ ID NO: 11)
5'-TTCACTGGCACATAGTTGAT-3'

(SEQ ID NO: 12)
5'-ACCTCTTGATTTTGGCGGTA-3'

(SEQ ID NO: 13)
5'-ATTCATTTGGGAGGAGATGA-3'

(SEQ ID NO: 14)
5'-GAAAGCATCACACTCTGACT-3'

(SEQ ID NO: 15)
5'-AATTTCTTTGAAAAATGTAG-3'

(SEQ ID NO: 16)
5'-TTATTGCTTAACTCAGGAAA-3'
```

Example 2: Hex Activity in the Culture Supernatant of a Modified Mod HEXB Expression Cell Strain The modified Mod HEXB expression vector produced in Example 1 was introduced into CHO cells with Lipofectamine 2000 (Invitrogen Corporation) and then a cell population which constitutively expressed the genes in the presence of neomycin derivative (G418 sulfate) and which has the drug resistance was selected. Subsequently, CHO clone cell lines highly expressing a modified Mod HEXB was established by limiting dilution method.

The obtained modified Mod HEXB expression cell strain was cultured in a serum containing medium (10% serum containing Ham's F-10) until it grew confluently. The resultant cell strain was subjected to passage culture in a serum free medium (EXCELL (Sigma)), and further cultured at 37° C., 5% $CO_2$ for 4 days.

Subsequently, the culture supernatant was recovered and subjected to centrifugation at 3000 rpm for 5 minutes, followed by recovering the supernatant.

The Hex activity of the obtained supernatant was obtained in such a way that 4-methylumbelliferyl-N-acetyl-β-D-glucosamine (4-MUG) and 4-methylumbelliferyl-6-sulfo-N-acetyl-β-D-glucosaminide (4-MUGS) were used as substrates, respectively, and the degradation activities of these substrates were estimated.

The result showed that the degradation activities of 4-MUG and 4-MUGS in the supernatant were 4160 nmol/h/mL and 1477 nmol/h/mL, respectively. The result indicates that these activities are comparable with the Hex activity in the culture supernatant of a Mod HEXB expression cell strain and the modified Mod HEXB retains the Hex activity.

Example 3: Assessment of the Protease Resistance of a Modified ModB

ConA sepharose (GE Healthcare) was used according to the manufacturer's instruction to concentrate and purify the culture supernatant of the modified Mod HEXB expression cell strain obtained in Example 2. Then, the concentrated and purified culture supernatant was electrophoretically migrated by SDS-PAGE and transcribed into a PVDF membrane using a semi-dry type transcription apparatus. The obtained membrane was blocked through Blocking One/TBS=1:1, followed by treating with a first probe (Anti-NAG (A): 1000-fold dilution), a second probe (Biotin-conjugated anti-rabbit IgG: 1000-fold dilution) and a third probe (HRP-conjugated anti-biotin: 1000-fold dilution) in order according to a conventionally known, general procedure. Subsequently, the modified ModB was detected through Western Lightning Plus-ECL (PerkinElmer Co., Ltd.). The culture supernatant of a Mod HEXB expression cell strain was detected as a control in a similar treatment manner. It is noted that Anti-NAG(A) used as the first probe is a polyclonal antibody recognizing both of the α- and β-subunit proteins of a human β-hexosaminidase A.

The results are shown in FIG. 2.

In a lane in which the Mod HEXB electrophoretically migrated, it was detected in the form degraded by protease at approximately 30 kDa. On the other hand, in a lane in which the modified Mod HEXB electrophoretically migrated, a band was not almost detected at approximately 30 kDa. This indicates that the modified Mod HEXB has high resistance to protease and the degradation by protease was remarkably suppressed.

Example 4: Assessment of the Thermal Stability of a Modified ModB

A modified Mod HEXB was purified from the culture supernatant of the modified Mod HEXB expression cell strain obtained in Example 2 through each of AF-Blue column (TOSOH, TOYOPEARL (registered mark) AF-Blue HC-650), Phos-tag column (WAKO, Phos-Tag (registered mark) Agarose) and SP column (GE Healthcare Life Science, HiTrap Sp-HP) according to the manufacturer's instruction. The culture supernatant of the Mod HEXB expression cell strain was purified as a control in the same manner to obtain a Mod HEXB.

Then, the purified modified Mod HEXB (1 μg of protein/lane) and Mod HEXB (2 μg of protein/lane) electrophoretically migrated through SDS-PAGE 10% acrylamide and stained with silver according to a conventionally known procedure to detect the modified Mod HEXB and Mod HEXB.

Figure 3:
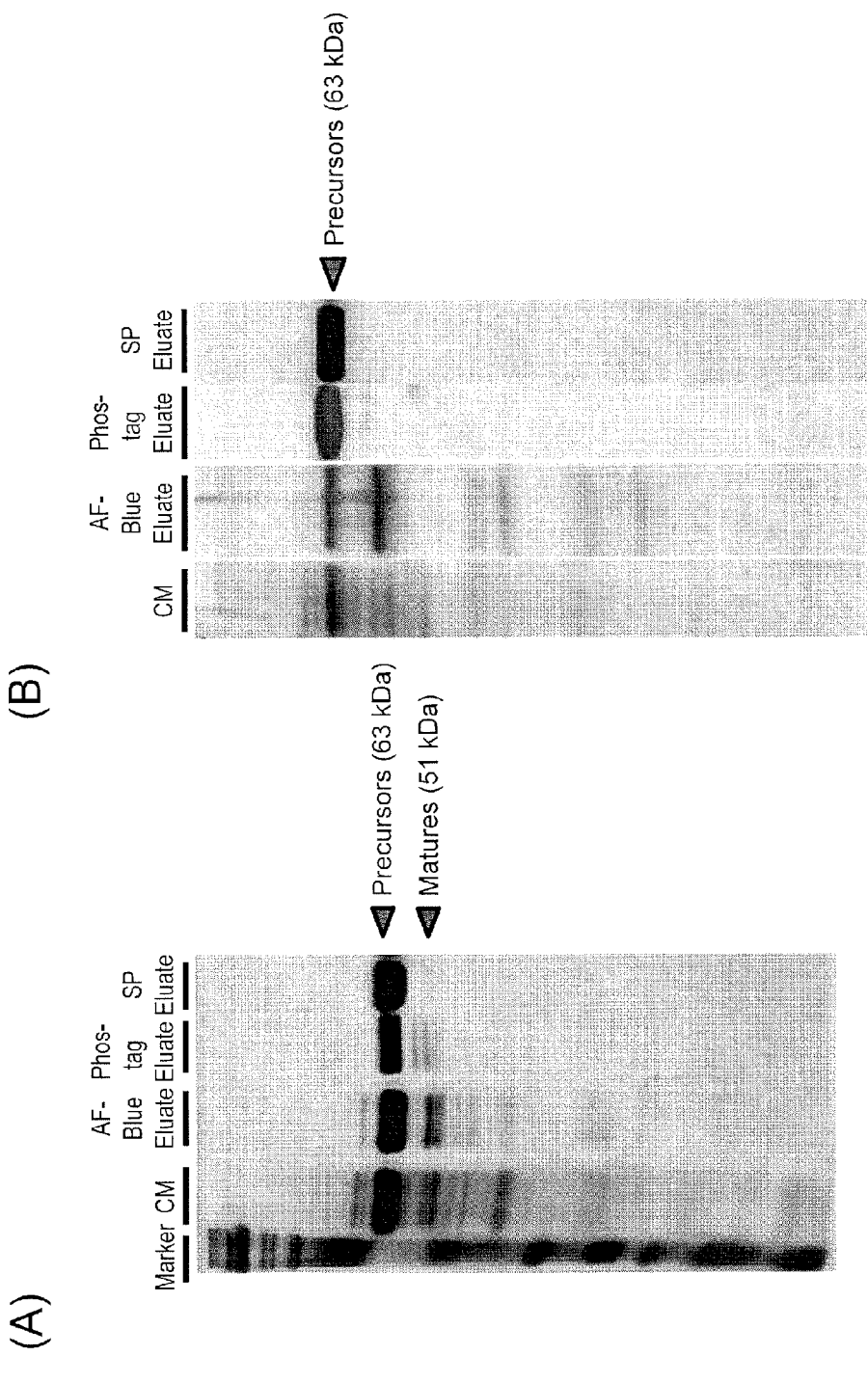
FIG. 3 is photographs showing detection results of (A) Mod HEXB and (B) modified Mod HEXB which were purified from a culture supernatant by silver staining.

The results are shown in FIG. 3.

In a lane in which the purified (A) Mod HEXB and the (B) modified Mod HEXB (SP Eluate) electrophoretically migrated, precursors of the proteins (approximately 63 kDa) were detected, while matures of the proteins (approximately 51 kDa) were not almost detected.

Then, the purified modified Mod HEXB (MUGS degradation activity, 2,000 nmol/h, 1 μg) and the Mod HEXB (MUGS degradation activity 2,000 nmol/h, 2 μg) were separately added to each sodium phosphate buffer (20 mM, pH 6.0) containing 30% (v/v) SD mouse plasma and each mixture was incubated at 37° C. Before the incubation and on days 2, 4 and 7 from the beginning of the incubation, the Hex activity in each solution was estimated with the degradation activity in which 4-MUGS served as a substrate.

Figure 4:
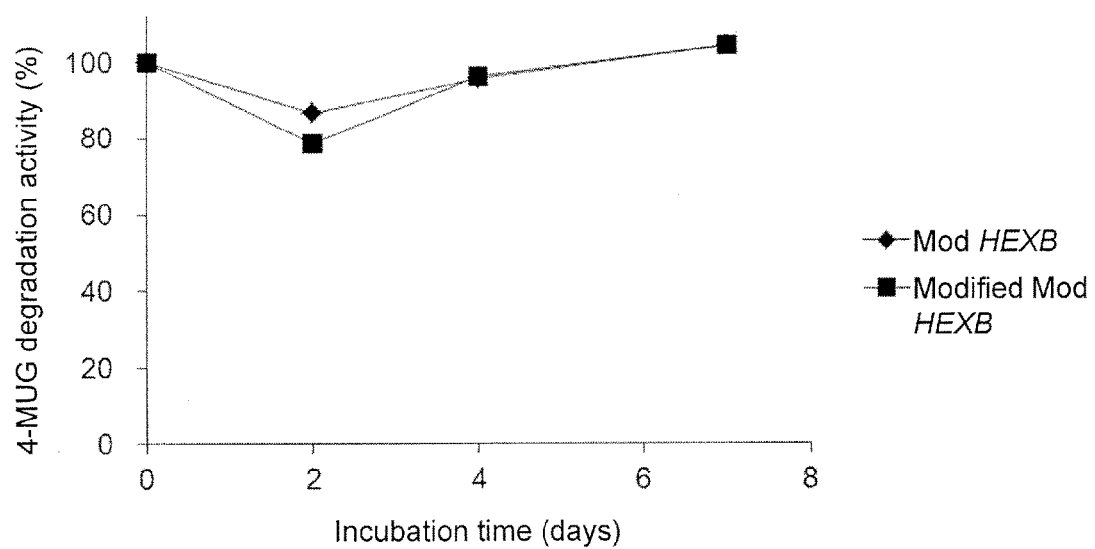
FIG. 4 is a graph showing the 4-MUGS degradation activity of the Mod HEXB and the modified Mod HEXB which were purified from a culture supernatant in the presence of plasma (protease). Each of values indicates relative activity to each of the 4-MUGS degradation activities of the Mod HEXB and the modified Mod HEXB in untreated forms, which are defined as 100%.

The results are shown in FIG. 4.

In the purified modified Mod HEXB, the 4-MUGS degradation activity was not decreased even in the incubation at pH 6.0 and 37° C. for 7 days in the presence of 30% (v/v) mouse plasma (including several proteases). This indicates that the modified Mod HEXB was not deactivated by heat-denaturation even under the above condition. The same results were confirmed in the purified Mod HEXB.

Example 5: Assessment of a Modified ModB Through the Administration to Sandhoff Disease Model Mice Sandhoff disease model mice aged 10 weeks old (4 cases assigned from [Dr. Richard L. Proia (Section on Biochemical Genetics, Genetics and Biochemistry Branch, National Institute of Diabetes and Digestive and Kidney Diseases)] were conditioned, followed by intraventricularly administrating the purified modified Mod HEXB obtained in Example 4 at a single dose of 1 mg/body weight kg and then motor functions of the mice aged 14, 15 and 16 weeks old were estimated by Rota-rod test. Controls were administered with PBS (n=12) or the purified Mod HEXB obtained in Example 4 (at a dose of 2 mg/body weight kg, n=12) in the same manner and then motor functions of the controls aged 14, 15 and 16 weeks old were estimated by Rota-rod test.

Figure 5:
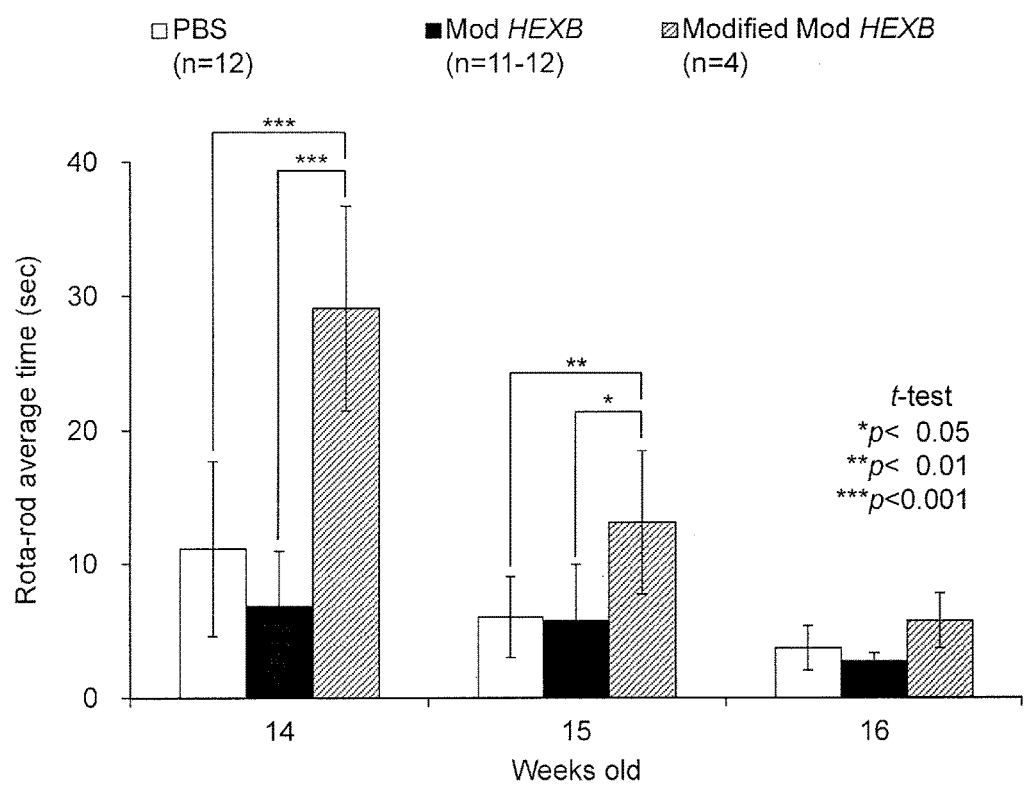
FIG. 5 is a graph showing results evaluated by Rota-rod test in motor functions of Sandhoff disease model mice aged 14 weeks or more and intraventricularly administered with the Mod HEXB or the modified Mod HEXB, each of which was purified from a culture supernatant.

The results are shown in FIG. 5.

In Sandhoff disease model mice which were administered with the modified Mod HEXB, the results indicated that their motor functional disorders, which were remarkably appeared at 14 weeks old or more, were significantly improved (delayed).

On the other hand, in Sandhoff disease model mice which were administered with a PBS or a Mod HEXB, the results indicated that their motor functional disorders were not improved.

These results indicate that the modified Mod HEXB is efficacious for treatments of Sandhoff disease and Tay-Sachs disease.

INDUSTRIAL APPLICABILITY

The present invention can provide a modified β-subunit which has the activity derived from the α-subunit of wild-type human β-hexosaminidase and has the resistance to protease. Since a modified β-hexosaminidase B which is a homodimer composed of the modified β-subunit retains the Hex activity and has the protease resistance as well as exhibits excellent stability in blood and cerebral spinal fluid, it is possible to utilize as an active component of high functional enzyme therapeutic agent for Sandhoff disease and Tay-Sachs disease. In particular, the modified β-hexosaminidase B does not contain an α-subunit and therefore, an adverse immune reaction is not likely caused even in administrating the modified β-hexosaminidase B to a patient with Tay-Sachs disease so that the modified β-hexosaminidase B is expected to contribute greatly to the treatment of the diseases.

All the publications, patents and patent applications cited herein are hereby incorporated by reference as they are.

What is claimed is:

1. A protein comprising an amino acid sequence of SEQ ID NO: 4, wherein the amino acid at positions 312 to 318 are substituted with glycine, serine, glutamic acid, proline, serine, glycine and threonine in order, respectively, and wherein the protein exhibits resistance to protease.

2. The protein according to claim 1, wherein the amino acid sequence of SEQ ID NO: 4 further comprises at least one other substitution: a substitution of the 452nd amino acid with asparagine, or a substitution of the 453rd amino acid with arginine.

3. The protein according to claim 2, wherein the amino acids at positions 312 to 318, 452 and 453 are identical to the respective amino acids of SEQ ID NO: 6.

4. A protein consisting of homodimers of the protein according to claim 1.

5. A gene encoding the protein according to claim 1.

6. A recombinant vector comprising the gene according to claim 5.

7. A transfectant comprising the recombinant vector according to claim 6.

8. A method for producing a protein having an activity derived from α-subunit of wild-type human β-hexosaminidase and having a resistance to protease comprising the steps of culturing the transfectant according to claim 7, and collecting the protein from the obtained culture.

9. The protein according to claim 2, wherein the protein is a fragment of the amino acid sequence of SEQ ID NO: 4, the fragment comprising the recited substitutions at positions 312 to 318, and at least one other recited substitution at position 452 or 453, and wherein the fragment has an activity derived from an α-subunit of wild-type human β-hexosaminidase.

10. The protein according to claim 2, wherein the amino acids at positions 312 to 318, 452 and 453 are identical to the respective amino acids of SEQ ID NO: 6, wherein the protein has at least 90% sequence identity to the amino acid sequence of SEQ ID NO: 6, and wherein the protein has an activity derived from the α-subunit of wild-type human β-hexosaminidase.

11. A protein consisting of homodimers of the protein according to claim 10.

12. A gene encoding the protein according to claim 10.

13. A recombinant vector comprising the gene according to claim 12.

14. A transfectant comprising the recombinant vector according to claim 13.

15. A method for producing a protein having an activity derived from α-subunit of wild-type human β-hexosaminidase and having a resistance to protease comprising the steps of:
    culturing the transfectant according to claim 14, and
    collecting the protein from the obtained culture.

\* \* \* \* \*

SEQUENCE LISTING

```
<160> NUMBER OF SEQ ID NOS: 17

<210> SEQ ID NO 1
<211> LENGTH: 1590
<212> TYPE: DNA
<213> ORGANISM: Homo sapiens
<220> FEATURE:
<221> NAME/KEY: CDS
<222> LOCATION: (1)..(1590)

<400> SEQUENCE: 1 atg aca agc tcc agg ctt tgg ttt tcg ctg ctg ctg gcg gca gcg ttc      48
Met Thr Ser Ser Arg Leu Trp Phe Ser Leu Leu Leu Ala Ala Ala Phe
1               5                   10                  15 gca gga cgg gcg acg gcc ctc tgg ccc tgg cct cag aac ttc caa acc      96
Ala Gly Arg Ala Thr Ala Leu Trp Pro Trp Pro Gln Asn Phe Gln Thr
                20                  25                  30 tcc gac cag cgc tac gtc ctt tac ccg aac aac ttt caa ttc cag tac     144
Ser Asp Gln Arg Tyr Val Leu Tyr Pro Asn Asn Phe Gln Phe Gln Tyr
            35                  40                  45 gat gtc agc tcg gcc gcg cag ccc ggc tgc tca gtc ctc gac gag gcc     192
Asp Val Ser Ser Ala Ala Gln Pro Gly Cys Ser Val Leu Asp Glu Ala
        50                  55                  60 ttc cag cgc tat cgt gac ctg ctt ttc ggt tcc ggg tct tgg ccc cgt     240
Phe Gln Arg Tyr Arg Asp Leu Leu Phe Gly Ser Gly Ser Trp Pro Arg
65                  70                  75                  80 cct tac ctc aca ggg aaa cgg cat aca ctg gag aag aat gtg ttg gtt     288
Pro Tyr Leu Thr Gly Lys Arg His Thr Leu Glu Lys Asn Val Leu Val
                85                  90                  95 gtc tct gta gtc aca cct gga tgt aac cag ctt cct act ttg gag tca     336
Val Ser Val Val Thr Pro Gly Cys Asn Gln Leu Pro Thr Leu Glu Ser
            100                 105                 110 gtg gag aat tat acc ctg acc ata aat gat gac cag tgt tta ctc ctc     384
Val Glu Asn Tyr Thr Leu Thr Ile Asn Asp Asp Gln Cys Leu Leu Leu
        115                 120                 125 tct gag act gtc tgg gga gct ctc cga ggt ctg gag act ttt agc cag     432
Ser Glu Thr Val Trp Gly Ala Leu Arg Gly Leu Glu Thr Phe Ser Gln
    130                 135                 140 ctt gtt tgg aaa tct gct gag ggc aca ttc ttt atc aac aag act gag     480
Leu Val Trp Lys Ser Ala Glu Gly Thr Phe Phe Ile Asn Lys Thr Glu
145                 150                 155                 160 att gag gac ttt ccc cgc ttt cct cac cgg ggc ttg ctg ttg gat aca     528
Ile Glu Asp Phe Pro Arg Phe Pro His Arg Gly Leu Leu Leu Asp Thr
                165                 170                 175 tct cgc cat tac ctg cca ctc tct agc atc ctg gac act ctg gat gtc     576
Ser Arg His Tyr Leu Pro Leu Ser Ser Ile Leu Asp Thr Leu Asp Val
            180                 185                 190 atg gcg tac aat aaa ttg aac gtg ttc cac tgg cat ctg gta gat gat     624
Met Ala Tyr Asn Lys Leu Asn Val Phe His Trp His Leu Val Asp Asp
        195                 200                 205 cct tcc ttc cca tat gag agc ttc act ttt cca gag ctc atg aga aag     672
Pro Ser Phe Pro Tyr Glu Ser Phe Thr Phe Pro Glu Leu Met Arg Lys
    210                 215                 220
```

```
ggg tcc tac aac cct gtc acc cac atc tac aca gca cag gat gtg aag    720
Gly Ser Tyr Asn Pro Val Thr His Ile Tyr Thr Ala Gln Asp Val Lys
225                 230                 235                 240 gag gtc att gaa tac gca cgg ctc cgg ggt atc cgt gtg ctt gca gag    768
Glu Val Ile Glu Tyr Ala Arg Leu Arg Gly Ile Arg Val Leu Ala Glu
                245                 250                 255 ttt gac act cct ggc cac act ttg tcc tgg gga cca ggt atc cct gga    816
Phe Asp Thr Pro Gly His Thr Leu Ser Trp Gly Pro Gly Ile Pro Gly
            260                 265                 270 tta ctg act cct tgc tac tct ggg tct gag ccc tct ggc acc ttt gga    864
Leu Leu Thr Pro Cys Tyr Ser Gly Ser Glu Pro Ser Gly Thr Phe Gly
        275                 280                 285 cca gtg aat ccc agt ctc aat aat acc tat gag ttc atg agc aca ttc    912
Pro Val Asn Pro Ser Leu Asn Asn Thr Tyr Glu Phe Met Ser Thr Phe
    290                 295                 300 ttc tta gaa gtc agc tct gtc ttc cca gat ttt tat ctt cat ctt gga    960
Phe Leu Glu Val Ser Ser Val Phe Pro Asp Phe Tyr Leu His Leu Gly
305                 310                 315                 320 gga gat gag gtt gat ttc acc tgc tgg aag tcc aac cca gag atc cag   1008
Gly Asp Glu Val Asp Phe Thr Cys Trp Lys Ser Asn Pro Glu Ile Gln
                325                 330                 335 gac ttt atg agg aag aaa ggc ttc ggt gag gac ttc aag cag ctg gag   1056
Asp Phe Met Arg Lys Lys Gly Phe Gly Glu Asp Phe Lys Gln Leu Glu
            340                 345                 350 tcc ttc tac atc cag acg ctg ctg gac atc gtc tct tct tat ggc aag   1104
Ser Phe Tyr Ile Gln Thr Leu Leu Asp Ile Val Ser Ser Tyr Gly Lys
        355                 360                 365 ggc tat gtg gtg tgg cag gag gtg ttt gat aat aaa gta aag att cag   1152
Gly Tyr Val Val Trp Gln Glu Val Phe Asp Asn Lys Val Lys Ile Gln
    370                 375                 380 cca gac aca atc ata cag gtg tgg cga gag gat att cca gtg aac tat   1200
Pro Asp Thr Ile Ile Gln Val Trp Arg Glu Asp Ile Pro Val Asn Tyr
385                 390                 395                 400 atg aag gag ctg gaa ctg gtc acc aag gcc ggc ttc cgg gcc ctt ctc   1248
Met Lys Glu Leu Glu Leu Val Thr Lys Ala Gly Phe Arg Ala Leu Leu
                405                 410                 415 tct gcc ccc tgg tac ctg aac cgt ata tcc tat ggc cct gac tgg aag   1296
Ser Ala Pro Trp Tyr Leu Asn Arg Ile Ser Tyr Gly Pro Asp Trp Lys
            420                 425                 430 gat ttc tac ata gtg gaa ccc ctg gca ttt gaa ggt acc cct gag cag   1344
Asp Phe Tyr Ile Val Glu Pro Leu Ala Phe Glu Gly Thr Pro Glu Gln
        435                 440                 445 aag gct ctg gtg att ggt gga gag gct tgt atg tgg gga gaa tat gtg   1392
Lys Ala Leu Val Ile Gly Gly Glu Ala Cys Met Trp Gly Glu Tyr Val
    450                 455                 460 gac aac aca aac ctg gtc ccc agg ctc tgg ccc aga gca ggg gct gtt   1440
Asp Asn Thr Asn Leu Val Pro Arg Leu Trp Pro Arg Ala Gly Ala Val
465                 470                 475                 480 gcc gaa agg ctg tgg agc aac aag ttg aca tct gac ctg aca ttt gcc   1488
Ala Glu Arg Leu Trp Ser Asn Lys Leu Thr Ser Asp Leu Thr Phe Ala
                485                 490                 495 tat gaa cgt ttg tca cac ttc cgc tgt gaa ttg ctg agg cga ggt gtc   1536
Tyr Glu Arg Leu Ser His Phe Arg Cys Glu Leu Leu Arg Arg Gly Val
            500                 505                 510 cag gcc caa ccc ctc aat gta ggc ttc tgt gag cag gag ttt gaa cag   1584
Gln Ala Gln Pro Leu Asn Val Gly Phe Cys Glu Gln Glu Phe Glu Gln
        515                 520                 525 acc tga                                                            1590
Thr
```

<210> SEQ ID NO 2
<211> LENGTH: 529
<212> TYPE: PRT
<213> ORGANISM: Homo sapiens

<400> SEQUENCE: 2

```
Met Thr Ser Ser Arg Leu Trp Phe Ser Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
            35                  40                  45

Asp Val Ser Ser Ala Ala Gln Pro Gly Cys Ser Val Leu Asp Glu Ala
            50                  55                  60

Phe Gln Arg Tyr Arg Asp Leu Leu Phe Gly Ser Gly Ser Trp Pro Arg
65              70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
                100                 105                 110

Val Glu Asn Tyr Thr Leu Thr Ile Asn Asp Asp Gln Cys Leu Leu Leu
            115                 120                 125

Ser Glu Thr Val Trp Gly Ala Leu Arg Gly Leu Glu Thr Phe Ser Gln
            130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
            195                 200                 205

Pro Ser Phe Pro Tyr Glu Ser Phe Thr Phe Pro Glu Leu Met Arg Lys
        210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
            275                 280                 285

Pro Val Asn Pro Ser Leu Asn Asn Thr Tyr Glu Phe Met Ser Thr Phe
        290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
            340                 345                 350

Ser Phe Tyr Ile Gln Thr Leu Leu Asp Ile Val Ser Ser Tyr Gly Lys
            355                 360                 365

Gly Tyr Val Val Trp Gln Glu Val Phe Asp Asn Lys Val Lys Ile Gln
```

```
              370                 375                 380
Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
                420                 425                 430

Asp Phe Tyr Ile Val Glu Pro Leu Ala Phe Glu Gly Thr Pro Glu Gln
                435                 440                 445

Lys Ala Leu Val Ile Gly Gly Glu Ala Cys Met Trp Gly Glu Tyr Val
                450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
                500                 505                 510

Gln Ala Gln Pro Leu Asn Val Gly Phe Cys Glu Gln Glu Phe Glu Gln
                515                 520                 525

Thr

<210> SEQ ID NO 3
<211> LENGTH: 1671
<212> TYPE: DNA
<213> ORGANISM: Homo sapiens
<220> FEATURE:
<221> NAME/KEY: CDS
<222> LOCATION: (1)..(1671)

<400> SEQUENCE: 3 atg gag ctg tgc ggg ctg ggg ctg ccc cgg ccg ccc atg ctg ctg gcg    48
Met Glu Leu Cys Gly Leu Gly Leu Pro Arg Pro Pro Met Leu Leu Ala
1               5                   10                  15 ctg ctg ttg gcg aca ctg ctg gcg gcg atg ttg gcg ctg ctg act cag    96
Leu Leu Leu Ala Thr Leu Leu Ala Ala Met Leu Ala Leu Leu Thr Gln
                20                  25                  30 gtg gcg ctg gtg gtg cag gtg gcg gag gcg gct cgg gcc ccg agc gtc   144
Val Ala Leu Val Val Gln Val Ala Glu Ala Ala Arg Ala Pro Ser Val
            35                  40                  45 tcg gcc aag ccg ggg ccg gcg ctg tgg ccc ctg ccg ctc tcg gtg aag   192
Ser Ala Lys Pro Gly Pro Ala Leu Trp Pro Leu Pro Leu Ser Val Lys
        50                  55                  60 atg acc ccg aac ctg ctg cat ctc gcc ccg gag aac ttc tac atc agc   240
Met Thr Pro Asn Leu Leu His Leu Ala Pro Glu Asn Phe Tyr Ile Ser
65                  70                  75                  80 cac agc ccc aat tcc acg gcg ggc ccc tcc tgc acc ctg ctg gag gaa   288
His Ser Pro Asn Ser Thr Ala Gly Pro Ser Cys Thr Leu Leu Glu Glu
                85                  90                  95 gcg ttt cga cga tat cat ggc tat att ttt ggt ttc tac aag tgg cat   336
Ala Phe Arg Arg Tyr His Gly Tyr Ile Phe Gly Phe Tyr Lys Trp His
                100                 105                 110 cat gaa cct gct gaa ttc cag gct aaa acc cag gtt cag caa ctt ctt   384
His Glu Pro Ala Glu Phe Gln Ala Lys Thr Gln Val Gln Gln Leu Leu
            115                 120                 125 gtc tca atc acc ctt cag tca gag tgt gat gct ttc ccc aac ata tct   432
Val Ser Ile Thr Leu Gln Ser Glu Cys Asp Ala Phe Pro Asn Ile Ser
        130                 135                 140 tca gat gag tct tat act tta ctt gtg aaa gaa cca gtg gct gtc ctt   480
```

```
Ser Asp Glu Ser Tyr Thr Leu Leu Val Lys Glu Pro Val Ala Val Leu
145                 150                 155                 160 aag gcc aac aga gtt tgg gga gca tta cga ggt tta gag acc ttt agc    528
Lys Ala Asn Arg Val Trp Gly Ala Leu Arg Gly Leu Glu Thr Phe Ser
                165                 170                 175 cag tta gtt tat caa gat tct tat gga act ttc acc atc aat gaa tcc    576
Gln Leu Val Tyr Gln Asp Ser Tyr Gly Thr Phe Thr Ile Asn Glu Ser
            180                 185                 190 acc att att gat tct cca agg ttt tct cac aga gga att ttg att gat    624
Thr Ile Ile Asp Ser Pro Arg Phe Ser His Arg Gly Ile Leu Ile Asp
        195                 200                 205 aca tcc aga cat tat ctg cca gtt aag att att ctt aaa act ctg gat    672
Thr Ser Arg His Tyr Leu Pro Val Lys Ile Ile Leu Lys Thr Leu Asp
    210                 215                 220 gcc atg gct ttt aat aag ttt aat gtt ctt cac tgg cac ata gtt gat    720
Ala Met Ala Phe Asn Lys Phe Asn Val Leu His Trp His Ile Val Asp
225                 230                 235                 240 gac cag tct ttc cca tat cag agc atc act ttt cct gag tta agc aat    768
Asp Gln Ser Phe Pro Tyr Gln Ser Ile Thr Phe Pro Glu Leu Ser Asn
                245                 250                 255 aaa gga agc tat tct ttg tct cat gtt tat aca cca aat gat gtc cgt    816
Lys Gly Ser Tyr Ser Leu Ser His Val Tyr Thr Pro Asn Asp Val Arg
            260                 265                 270 atg gtg att gaa tat gcc aga tta cga gga att cga gtc ctg cca gaa    864
Met Val Ile Glu Tyr Ala Arg Leu Arg Gly Ile Arg Val Leu Pro Glu
        275                 280                 285 ttt gat acc cct ggg cat aca cta tct tgg gga aaa ggt cag aaa gac    912
Phe Asp Thr Pro Gly His Thr Leu Ser Trp Gly Lys Gly Gln Lys Asp
    290                 295                 300 ctc ctg act cca tgt tac agt aga caa aac aag ttg gac tct ttt gga    960
Leu Leu Thr Pro Cys Tyr Ser Arg Gln Asn Lys Leu Asp Ser Phe Gly
305                 310                 315                 320 cct ata aac cct act ctg aat aca aca tac agc ttc ctt act aca ttt   1008
Pro Ile Asn Pro Thr Leu Asn Thr Thr Tyr Ser Phe Leu Thr Thr Phe
                325                 330                 335 ttc aaa gaa att agt gag gtg ttt cca gat caa ttc att cat ttg gga   1056
Phe Lys Glu Ile Ser Glu Val Phe Pro Asp Gln Phe Ile His Leu Gly
            340                 345                 350 gga gat gaa gtg gaa ttt aaa tgt tgg gaa tca aat cca aaa att caa   1104
Gly Asp Glu Val Glu Phe Lys Cys Trp Glu Ser Asn Pro Lys Ile Gln
        355                 360                 365 gat ttc atg agg caa aaa ggc ttt ggc aca gat ttt aag aaa cta gaa   1152
Asp Phe Met Arg Gln Lys Gly Phe Gly Thr Asp Phe Lys Lys Leu Glu
    370                 375                 380 tct ttc tac att caa aag gtt ttg gat att att gca acc ata aac aag   1200
Ser Phe Tyr Ile Gln Lys Val Leu Asp Ile Ile Ala Thr Ile Asn Lys
385                 390                 395                 400 gga tcc att gtc tgg cag gag gtt ttt gat gat aaa gca aag ctt gcg   1248
Gly Ser Ile Val Trp Gln Glu Val Phe Asp Asp Lys Ala Lys Leu Ala
                405                 410                 415 ccg ggc aca ata gtt gaa gta tgg aaa gac agc gca tat cct gag gaa   1296
Pro Gly Thr Ile Val Glu Val Trp Lys Asp Ser Ala Tyr Pro Glu Glu
            420                 425                 430 ctc agt aga gtc aca gca tct ggc ttc cct gta atc ctt tct gct cct   1344
Leu Ser Arg Val Thr Ala Ser Gly Phe Pro Val Ile Leu Ser Ala Pro
        435                 440                 445 tgg tac tta gat ttg att agc tat gga caa gat tgg agg aaa tac tat   1392
Trp Tyr Leu Asp Leu Ile Ser Tyr Gly Gln Asp Trp Arg Lys Tyr Tyr
    450                 455                 460
```

```
aaa gtg gaa cct ctt gat ttt ggc ggt act cag aaa cag aaa caa ctt    1440
Lys Val Glu Pro Leu Asp Phe Gly Gly Thr Gln Lys Gln Lys Gln Leu
465                 470                 475                 480 ttc att ggt gga gaa gct tgt cta tgg gga gaa tat gtg gat gca act    1488
Phe Ile Gly Gly Glu Ala Cys Leu Trp Gly Glu Tyr Val Asp Ala Thr
                485                 490                 495 aac ctc act cca aga tta tgg cct cgg gca agt gct gtt ggt gag aga    1536
Asn Leu Thr Pro Arg Leu Trp Pro Arg Ala Ser Ala Val Gly Glu Arg
            500                 505                 510 ctc tgg agt tcc aaa gat gtc aga gat atg gat gac gcc tat gac aga    1584
Leu Trp Ser Ser Lys Asp Val Arg Asp Met Asp Asp Ala Tyr Asp Arg
        515                 520                 525 ctg aca agg cac cgc tgc agg atg gtc gaa cgt gga ata gct gca caa    1632
Leu Thr Arg His Arg Cys Arg Met Val Glu Arg Gly Ile Ala Ala Gln
    530                 535                 540 cct ctt tat gct gga tat tgt aac cat gag aac atg taa                1671
Pro Leu Tyr Ala Gly Tyr Cys Asn His Glu Asn Met
545                 550                 555
```

<210> SEQ ID NO 4
<211> LENGTH: 556
<212> TYPE: PRT
<213> ORGANISM: Homo sapiens

<400> SEQUENCE: 4

```
Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
                20                  25                  30

Val Ala Leu Val Val Gln Val Ala Glu Ala Ala Arg Ala Pro Ser Val
            35                  40                  45

Ser Ala Lys Pro Gly Pro Ala Leu Trp Pro Leu Pro Leu Ser Val Lys
        50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
                100                 105                 110

His Glu Pro Ala Glu Phe Gln Ala Lys Thr Gln Val Gln Gln Leu Leu
            115                 120                 125

Val Ser Ile Thr Leu Gln Ser Glu Cys Asp Ala Phe Pro Asn Ile Ser
        130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
            180                 185                 190

Thr Ile Ile Asp Ser Pro Arg Phe Ser His Arg Gly Ile Leu Ile Asp
        195                 200                 205

Thr Ser Arg His Tyr Leu Pro Val Lys Ile Ile Leu Lys Thr Leu Asp
    210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255
```

```
Lys Gly Ser Tyr Ser Leu Ser His Val Tyr Thr Pro Asn Asp Val Arg
            260                 265                 270

Met Val Ile Glu Tyr Ala Arg Leu Arg Gly Ile Arg Val Leu Pro Glu
            275                 280                 285

Phe Asp Thr Pro Gly His Thr Leu Ser Trp Lys Gly Gln Lys Asp
            290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                    325                 330                 335

Phe Lys Glu Ile Ser Glu Val Phe Pro Asp Gln Phe Ile His Leu Gly
                    340                 345                 350

Gly Asp Glu Val Glu Phe Lys Cys Trp Glu Ser Asn Pro Lys Ile Gln
                    355                 360                 365

Asp Phe Met Arg Gln Lys Gly Phe Gly Thr Asp Phe Lys Lys Leu Glu
            370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Asp Lys Ala Lys Leu Ala
                    405                 410                 415

Pro Gly Thr Ile Val Glu Val Trp Lys Asp Ser Ala Tyr Pro Glu Glu
                    420                 425                 430

Leu Ser Arg Val Thr Ala Ser Gly Phe Pro Val Ile Leu Ser Ala Pro
            435                 440                 445

Trp Tyr Leu Asp Leu Ile Ser Tyr Gly Gln Asp Trp Arg Lys Tyr Tyr
            450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                    485                 490                 495

Asn Leu Thr Pro Arg Leu Trp Pro Arg Ala Ser Ala Val Gly Glu Arg
            500                 505                 510

Leu Trp Ser Ser Lys Asp Val Arg Asp Met Asp Asp Ala Tyr Asp Arg
            515                 520                 525

Leu Thr Arg His Arg Cys Arg Met Val Glu Arg Gly Ile Ala Ala Gln
            530                 535                 540

Pro Leu Tyr Ala Gly Tyr Cys Asn His Glu Asn Met
545                 550                 555

<210> SEQ ID NO 5
<211> LENGTH: 1671
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(1671)

<400> SEQUENCE: 5 atg gag ctg tgc ggg ctg ggg ctg ccc cgg ccg ccc atg ctg ctg gcg      48
Met Glu Leu Cys Gly Leu Gly Leu Pro Arg Pro Pro Met Leu Leu Ala
1               5                   10                  15 ctg ctg ttg gcg aca ctg ctg gcg gcg atg ttg gcg ctg ctg act cag      96
Leu Leu Leu Ala Thr Leu Leu Ala Ala Met Leu Ala Leu Leu Thr Gln
            20                  25                  30
```

-continued

| | | |
|---|---|---|
| gtg gcg ctg gtg gtg cag gtg gcg gag gcg gct cgg gcc ccg agc gtc<br>Val Ala Leu Val Val Gln Val Ala Glu Ala Ala Arg Ala Pro Ser Val<br>35                    40                  45 | 144 | |
| tcg gcc aag ccg ggg ccg gcg ctg tgg ccc ctg ccg ctc tcg gtg aag<br>Ser Ala Lys Pro Gly Pro Ala Leu Trp Pro Leu Pro Leu Ser Val Lys<br>50                      55                  60 | 192 | |
| atg acc ccg aac ctg ctg cat ctc gcc ccg gag aac ttc tac atc agc<br>Met Thr Pro Asn Leu Leu His Leu Ala Pro Glu Asn Phe Tyr Ile Ser<br>65                    70                  75                  80 | 240 | |
| cac agc ccc aat tcc acg gcg ggc ccc tcc tgc acc ctg ctg gag gaa<br>His Ser Pro Asn Ser Thr Ala Gly Pro Ser Cys Thr Leu Leu Glu Glu<br>                    85                  90                  95 | 288 | |
| gcg ttt cga cga tat cat ggc tat att ttt ggt ttc tac aag tgg cat<br>Ala Phe Arg Arg Tyr His Gly Tyr Ile Phe Gly Phe Tyr Lys Trp His<br>                  100                105                110 | 336 | |
| cat gaa cct gct gaa ttc cag gct aaa acc cag gtt cag caa ctt ctt<br>His Glu Pro Ala Glu Phe Gln Ala Lys Thr Gln Val Gln Gln Leu Leu<br>                  115                120                125 | 384 | |
| gtc tca atc acc ctt cag tca gag tgt gat gct ttc ccc aac ata tct<br>Val Ser Ile Thr Leu Gln Ser Glu Cys Asp Ala Phe Pro Asn Ile Ser<br>130                    135                140 | 432 | |
| tca gat gag tct tat act tta ctt gtg aaa gaa cca gtg gct gtc ctt<br>Ser Asp Glu Ser Tyr Thr Leu Leu Val Lys Glu Pro Val Ala Val Leu<br>145                    150                155                160 | 480 | |
| aag gcc aac aga gtt tgg gga gca tta cga ggt tta gag acc ttt agc<br>Lys Ala Asn Arg Val Trp Gly Ala Leu Arg Gly Leu Glu Thr Phe Ser<br>                  165                170                175 | 528 | |
| cag tta gtt tat caa gat tct tat gga act ttc acc atc aat gaa tcc<br>Gln Leu Val Tyr Gln Asp Ser Tyr Gly Thr Phe Thr Ile Asn Glu Ser<br>                  180                185                190 | 576 | |
| acc att att gat tct cca agg ttt tct cac aga gga att ttg att gat<br>Thr Ile Ile Asp Ser Pro Arg Phe Ser His Arg Gly Ile Leu Ile Asp<br>                    195                200                205 | 624 | |
| aca tcc aga cat tat ctg cca gtt aag att att ctt aaa act ctg gat<br>Thr Ser Arg His Tyr Leu Pro Val Lys Ile Ile Leu Lys Thr Leu Asp<br>210                    215                220 | 672 | |
| gcc atg gct ttt aat aag ttt aat gtt ctt cac tgg cac ata gtt gat<br>Ala Met Ala Phe Asn Lys Phe Asn Val Leu His Trp His Ile Val Asp<br>225                  230                235                240 | 720 | |
| gac cag tct ttc cca tat cag agc atc act ttt cct gag tta agc aat<br>Asp Gln Ser Phe Pro Tyr Gln Ser Ile Thr Phe Pro Glu Leu Ser Asn<br>                  245                250                255 | 768 | |
| aaa gga agc tat tct ttg tct cat gtt tat aca cca aat gat gtc cgt<br>Lys Gly Ser Tyr Ser Leu Ser His Val Tyr Thr Pro Asn Asp Val Arg<br>                  260                265                270 | 816 | |
| atg gtg att gaa tat gcc aga tta cga gga att cga gtc ctg cca gaa<br>Met Val Ile Glu Tyr Ala Arg Leu Arg Gly Ile Arg Val Leu Pro Glu<br>                  275                280                285 | 864 | |
| ttt gat acc cct ggg cat aca cta tct tgg gga aaa ggt cag aaa gac<br>Phe Asp Thr Pro Gly His Thr Leu Ser Trp Gly Lys Gly Gln Lys Asp<br>                  290                295                300 | 912 | |
| ctc ctg act cca tgt tac agt ggg tct gag ccc tct ggc acc ttt gga<br>Leu Leu Thr Pro Cys Tyr Ser Gly Ser Glu Pro Ser Gly Thr Phe Gly<br>305                    310                315                320 | 960 | |
| cct ata aac cct act ctg aat aca aca tac agc ttc ctt act aca ttt<br>Pro Ile Asn Pro Thr Leu Asn Thr Thr Tyr Ser Phe Leu Thr Thr Phe<br>                  325                330                335 | 1008 | |
| ttc aaa gaa att agt gag gtg ttt cca gat caa ttc att cat ttg gga<br>Phe Lys Glu Ile Ser Glu Val Phe Pro Asp Gln Phe Ile His Leu Gly<br>                  340                345                350 | 1056 | |

-continued

```
gga gat gaa gtg gaa ttt aaa tgt tgg gaa tca aat cca aaa att caa      1104
Gly Asp Glu Val Glu Phe Lys Cys Trp Glu Ser Asn Pro Lys Ile Gln
        355                 360                 365 gat ttc atg agg caa aaa ggc ttt ggc aca gat ttt aag aaa cta gaa      1152
Asp Phe Met Arg Gln Lys Gly Phe Gly Thr Asp Phe Lys Lys Leu Glu
    370                 375                 380 tct ttc tac att caa aag gtt ttg gat att att gca acc ata aac aag      1200
Ser Phe Tyr Ile Gln Lys Val Leu Asp Ile Ile Ala Thr Ile Asn Lys
385                 390                 395                 400 gga tcc att gtc tgg cag gag gtt ttt gat gat aaa gca aag ctt gcg      1248
Gly Ser Ile Val Trp Gln Glu Val Phe Asp Asp Lys Ala Lys Leu Ala
            405                 410                 415 ccg ggc aca ata gtt gaa gta tgg aaa gac agc gca tat cct gag gaa      1296
Pro Gly Thr Ile Val Glu Val Trp Lys Asp Ser Ala Tyr Pro Glu Glu
        420                 425                 430 ctc agt aga gtc aca gca tct ggc ttc cct gta atc ctt tct gct cct      1344
Leu Ser Arg Val Thr Ala Ser Gly Phe Pro Val Ile Leu Ser Ala Pro
    435                 440                 445 tgg tac tta aac cgt att agc tat gga caa gat tgg agg aaa tac tat      1392
Trp Tyr Leu Asn Arg Ile Ser Tyr Gly Gln Asp Trp Arg Lys Tyr Tyr
450                 455                 460 aaa gtg gaa cct ctt gat ttt gcc ggt act cag aaa cag aaa caa ctt      1440
Lys Val Glu Pro Leu Asp Phe Gly Gly Thr Gln Lys Gln Lys Gln Leu
465                 470                 475                 480 ttc att ggt gga gaa gct tgt cta tgg gga gaa tat gtg gat gca act      1488
Phe Ile Gly Gly Glu Ala Cys Leu Trp Gly Glu Tyr Val Asp Ala Thr
            485                 490                 495 aac ctc act cca aga tta tgg cct cgg gca agt gct gtt ggt gag aga      1536
Asn Leu Thr Pro Arg Leu Trp Pro Arg Ala Ser Ala Val Gly Glu Arg
        500                 505                 510 ctc tgg agt tcc aaa gat gtc aga gat atg gat gac gcc tat gac aga      1584
Leu Trp Ser Ser Lys Asp Val Arg Asp Met Asp Asp Ala Tyr Asp Arg
    515                 520                 525 ctg aca agg cac cgc tgc agg atg gtc gaa cgt gga ata gct gca caa      1632
Leu Thr Arg His Arg Cys Arg Met Val Glu Arg Gly Ile Ala Ala Gln
530                 535                 540 cct ctt tat gct gga tat tgt aac cat gag aac atg taa                  1671
Pro Leu Tyr Ala Gly Tyr Cys Asn His Glu Asn Met
545                 550                 555
```

<210> SEQ ID NO 6
<211> LENGTH: 556
<212> TYPE: PRT
<213> ORGANISM: Artificial
<220> FEATURE:
<223> OTHER INFORMATION: recombinant protein

<400> SEQUENCE: 6

```
Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
                20                  25                  30

Val Ala Leu Val Val Gln Val Ala Glu Ala Ala Arg Ala Pro Ser Val
            35                  40                  45

Ser Ala Lys Pro Gly Pro Ala Leu Trp Pro Leu Pro Leu Ser Val Lys
        50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
```

```
            85                  90                  95
Ala Phe Arg Arg Tyr His Gly Tyr Ile Phe Gly Phe Tyr Lys Trp His
            100                 105                 110

His Glu Pro Ala Glu Phe Gln Ala Lys Thr Gln Val Gln Gln Leu Leu
            115                 120                 125

Val Ser Ile Thr Leu Gln Ser Glu Cys Asp Ala Phe Pro Asn Ile Ser
        130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
            180                 185                 190

Thr Ile Ile Asp Ser Pro Arg Phe Ser His Arg Gly Ile Leu Ile Asp
            195                 200                 205

Thr Ser Arg His Tyr Leu Pro Val Lys Ile Ile Leu Lys Thr Leu Asp
        210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
            260                 265                 270

Met Val Ile Glu Tyr Ala Arg Leu Arg Gly Ile Arg Val Leu Pro Glu
            275                 280                 285

Phe Asp Thr Pro Gly His Thr Leu Ser Trp Gly Lys Gly Gln Lys Asp
        290                 295                 300

Leu Leu Thr Pro Cys Tyr Ser Gly Ser Glu Pro Ser Gly Thr Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
            340                 345                 350

Gly Asp Glu Val Glu Phe Lys Cys Trp Glu Ser Asn Pro Lys Ile Gln
            355                 360                 365

Asp Phe Met Arg Gln Lys Gly Phe Gly Thr Asp Phe Lys Lys Leu Glu
        370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Asp Lys Ala Lys Leu Ala
                405                 410                 415

Pro Gly Thr Ile Val Glu Val Trp Lys Asp Ser Ala Tyr Pro Glu Glu
            420                 425                 430

Leu Ser Arg Val Thr Ala Ser Gly Phe Pro Val Ile Leu Ser Ala Pro
            435                 440                 445

Trp Tyr Leu Asn Arg Ile Ser Tyr Gly Gln Asp Trp Arg Lys Tyr Tyr
        450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
            500                 505                 510
```

```
Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
        530                 535                 540

Pro Leu Tyr Ala Gly Tyr Cys Asn His Glu Asn Met
545                 550                 555
```

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
aaagaattcc tcgagcacca tgctgctggc gctg                                34

<210> SEQ ID NO 8
<211> LENGTH: 39
<212> TYPE: DNA
<213> ORGANISM: Artificial
<220> FEATURE:
<223> OTHER INFORMATION: primer

<400> SEQUENCE: 8
ggtgccagag ggctcagacc cactgtaaca tggagtcag                           39

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
gagccctctg gcacctttgg acctataaac                                     30

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
gagggaaaaa gatcttacat gttctcatg                                      29

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ttcactggca catagttgat                                                20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12

```
acctcttgat tttggcggta                                              20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
attcatttgg gaggagatga                                              20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
gaaagcatca cactctgact                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
aatttctttg aaaaatgtag                                              20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
ttattgctta actcaggaaa                                              20

<210> SEQ ID NO 17
<211> LENGTH: 1671
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(1671)

<400> SEQUENCE: 17 atg gag ctg tgc ggg ctg ggg ctg ccc cgg ccg ccc atg ctg ctg gcg     48
Met Glu Leu Cys Gly Leu Gly Leu Pro Arg Pro Pro Met Leu Leu Ala
 1               5                  10                  15 ctg ctg ttg gcg aca ctg ctg gcg gcg atg ttg gcg ctg ctg act cag     96
Leu Leu Leu Ala Thr Leu Leu Ala Ala Met Leu Ala Leu Leu Thr Gln
             20                  25                  30 gtg gcg ctg gtg gtg cag gtg gcg gag gcg gct cgg gcc ccg agc gtc    144
Val Ala Leu Val Val Gln Val Ala Glu Ala Ala Arg Ala Pro Ser Val
         35                  40                  45 tcg gcc aag ccg ggg ccg gcg ctg tgg ccc ctg ccg ctc tcg gtg aag    192
Ser Ala Lys Pro Gly Pro Ala Leu Trp Pro Leu Pro Leu Ser Val Lys
     50                  55                  60
```

```
atg acc ccg aac ctg ctg cat ctc gcc ccg gag aac ttc tac atc agc      240
Met Thr Pro Asn Leu Leu His Leu Ala Pro Glu Asn Phe Tyr Ile Ser
65              70                  75                  80 cac agc ccc aat tcc acg gcg ggc ccc tcc tgc acc ctg ctg gag gaa      288
His Ser Pro Asn Ser Thr Ala Gly Pro Ser Cys Thr Leu Leu Glu Glu
                85                  90                  95 gcg ttt cga cga tat cat ggc tat att ttt ggt ttc tac aag tgg cat      336
Ala Phe Arg Arg Tyr His Gly Tyr Ile Phe Gly Phe Tyr Lys Trp His
            100                 105                 110 cat gaa cct gct gaa ttc cag gct aaa acc cag gtt cag caa ctt ctt      384
His Glu Pro Ala Glu Phe Gln Ala Lys Thr Gln Val Gln Gln Leu Leu
        115                 120                 125 gtc tca atc acc ctt cag tca gag tgt gat gct ttc ccc aac ata tct      432
Val Ser Ile Thr Leu Gln Ser Glu Cys Asp Ala Phe Pro Asn Ile Ser
    130                 135                 140 tca gat gag tct tat act tta ctt gtg aaa gaa cca gtg gct gtc ctt      480
Ser Asp Glu Ser Tyr Thr Leu Leu Val Lys Glu Pro Val Ala Val Leu
145                 150                 155                 160 aag gcc aac aga gtt tgg gga gca tta cga ggt tta gag acc ttt agc      528
Lys Ala Asn Arg Val Trp Gly Ala Leu Arg Gly Leu Glu Thr Phe Ser
                165                 170                 175 cag tta gtt tat caa gat tct tat gga act ttc acc atc aat gaa tcc      576
Gln Leu Val Tyr Gln Asp Ser Tyr Gly Thr Phe Thr Ile Asn Glu Ser
            180                 185                 190 acc att att gat tct cca agg ttt tct cac aga gga att ttg att gat      624
Thr Ile Ile Asp Ser Pro Arg Phe Ser His Arg Gly Ile Leu Ile Asp
        195                 200                 205 aca tcc aga cat tat ctg cca gtt aag att att ctt aaa act ctg gat      672
Thr Ser Arg His Tyr Leu Pro Val Lys Ile Ile Leu Lys Thr Leu Asp
    210                 215                 220 gcc atg gct ttt aat aag ttt aat gtt ctt cac tgg cac ata gtt gat      720
Ala Met Ala Phe Asn Lys Phe Asn Val Leu His Trp His Ile Val Asp
225                 230                 235                 240 gac cag tct ttc cca tat cag agc atc act ttt cct gag tta agc aat      768
Asp Gln Ser Phe Pro Tyr Gln Ser Ile Thr Phe Pro Glu Leu Ser Asn
                245                 250                 255 aaa gga agc tat tct ttg tct cat gtt tat aca cca aat gat gtc cgt      816
Lys Gly Ser Tyr Ser Leu Ser His Val Tyr Thr Pro Asn Asp Val Arg
            260                 265                 270 atg gtg att gaa tat gcc aga tta cga gga att cga gtc ctg cca gaa      864
Met Val Ile Glu Tyr Ala Arg Leu Arg Gly Ile Arg Val Leu Pro Glu
        275                 280                 285 ttt gat acc cct ggg cat aca cta tct tgg gga aaa ggt cag aaa gac      912
Phe Asp Thr Pro Gly His Thr Leu Ser Trp Gly Lys Gly Gln Lys Asp
    290                 295                 300 ctc ctg act cca tgt tac agt ggg tct gag ccc ttg gac tct ttt gga      960
Leu Leu Thr Pro Cys Tyr Ser Gly Ser Glu Pro Leu Asp Ser Phe Gly
305                 310                 315                 320 cct ata aac cct act ctg aat aca aca tac agc ttc ctt act aca ttt     1008
Pro Ile Asn Pro Thr Leu Asn Thr Thr Tyr Ser Phe Leu Thr Thr Phe
                325                 330                 335 ttc aaa gaa att agt gag gtg ttt cca gat caa ttc att cat ttg gga     1056
Phe Lys Glu Ile Ser Glu Val Phe Pro Asp Gln Phe Ile His Leu Gly
            340                 345                 350 gga gat gaa gtg gaa ttt aaa tgt tgg gaa tca aat cca aaa att caa     1104
Gly Asp Glu Val Glu Phe Lys Cys Trp Glu Ser Asn Pro Lys Ile Gln
        355                 360                 365 gat ttc atg agg caa aaa ggc ttt ggc aca gat ttt aag aaa cta gaa     1152
Asp Phe Met Arg Gln Lys Gly Phe Gly Thr Asp Phe Lys Lys Leu Glu
```

```
        370                 375                 380
tct ttc tac att caa aag gtt ttg gat att att gca acc ata aac aag      1200
Ser Phe Tyr Ile Gln Lys Val Leu Asp Ile Ile Ala Thr Ile Asn Lys
385                 390                 395                 400 gga tcc att gtc tgg cag gag gtt ttt gat gat aaa gca aag ctt gcg      1248
Gly Ser Ile Val Trp Gln Glu Val Phe Asp Asp Lys Ala Lys Leu Ala
                    405                 410                 415 ccg ggc aca ata gtt gaa gta tgg aaa gac agc gca tat cct gag gaa      1296
Pro Gly Thr Ile Val Glu Val Trp Lys Asp Ser Ala Tyr Pro Glu Glu
                420                 425                 430 ctc agt aga gtc aca gca tct ggc ttc cct gta atc ctt tct gct cct      1344
Leu Ser Arg Val Thr Ala Ser Gly Phe Pro Val Ile Leu Ser Ala Pro
            435                 440                 445 tgg tac tta aac cgt att agc tat gga caa gat tgg agg aaa tac tat      1392
Trp Tyr Leu Asn Arg Ile Ser Tyr Gly Gln Asp Trp Arg Lys Tyr Tyr
        450                 455                 460 aaa gtg gaa cct ctt gat ttt ggc ggt act cag aaa cag aaa caa ctt      1440
Lys Val Glu Pro Leu Asp Phe Gly Gly Thr Gln Lys Gln Lys Gln Leu
465                 470                 475                 480 ttc att ggt gga gaa gct tgt cta tgg gga gaa tat gtg gat gca act      1488
Phe Ile Gly Gly Glu Ala Cys Leu Trp Gly Glu Tyr Val Asp Ala Thr
                485                 490                 495 aac ctc act cca aga tta tgg cct cgg gca agt gct gtt ggt gag aga      1536
Asn Leu Thr Pro Arg Leu Trp Pro Arg Ala Ser Ala Val Gly Glu Arg
            500                 505                 510 ctc tgg agt tcc aaa gat gtc aga gat atg gat gac gcc tat gac aga      1584
Leu Trp Ser Ser Lys Asp Val Arg Asp Met Asp Asp Ala Tyr Asp Arg
        515                 520                 525 ctg aca agg cac cgc tgc agg atg gtc gaa cgt gga ata gct gca caa      1632
Leu Thr Arg His Arg Cys Arg Met Val Glu Arg Gly Ile Ala Ala Gln
    530                 535                 540 cct ctt tat gct gga tat tgt aac cat gag aac atg taa                  1671
Pro Leu Tyr Ala Gly Tyr Cys Asn His Glu Asn Met
545                 550                 555
```